United States Patent
Popescu

(10) Patent No.: US 11,101,025 B2
(45) Date of Patent: *Aug. 24, 2021

(54) PROVIDING A PATIENT MODEL OF A PATIENT

(71) Applicant: Siemens Healthcare GmbH, Erlangen (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 92 days.

This patent is subject to a terminal disclaimer.

(21) Appl. No.: 16/653,134

(22) Filed: Oct. 15, 2019

(65) Prior Publication Data

US 2020/0043581 A1    Feb. 6, 2020

Related U.S. Application Data

(63) Continuation of application No. 16/202,405, filed on Nov. 28, 2018, now Pat. No. 10,497,469.

(30) Foreign Application Priority Data

Dec. 1, 2017    (DE) .................. 102017221720.0

(51) Int. Cl.
*G16H 30/40* (2018.01)
*G16H 10/60* (2018.01)
(Continued)

(52) U.S. Cl.
CPC ............ *G16H 10/60* (2018.01); *A61B 5/055* (2013.01); *A61B 6/4417* (2013.01); *A61B 90/00* (2016.02);
(Continued)

(58) Field of Classification Search
CPC ... G16H 10/60; G16H 30/40; G06Q 50/22–24
See application file for complete search history.

(56) References Cited

U.S. PATENT DOCUMENTS 6,421,551 B1 *   7/2002   Kuth ................. G01R 33/5673
                                                                324/307
6,895,268 B1 *   5/2005   Rahn ..................... G03B 42/02
                                                                378/20
(Continued)

FOREIGN PATENT DOCUMENTS

WO    WO-2011070464 A2 *  6/2011  ............ G06T 7/149

OTHER PUBLICATIONS

German Office Action for German Application No. 102017221720.0 dated Sep. 9, 2018.

(Continued)

*Primary Examiner* — John A Pauls
(74) *Attorney, Agent, or Firm* — Harness, Dickey & Pierce, P.L.C.

(57) ABSTRACT

A method includes receiving a first patient model of the patient, the first patient model including a first image dataset of the patient, the first image dataset being coordinated relative to a first coordinate system; receiving a second image dataset of the patient, the second image dataset being based on a medical imaging apparatus and being coordinated relative to a second coordinate system; determining a transformation function to transfer the second coordinate system into the first coordinate system; determining a transformed second image dataset based on the second image dataset and the transformation function; and providing a second patient model of the patient, the second patient model including the modified first image dataset.

24 Claims, 7 Drawing Sheets

(51) Int. Cl.

| | |
|---|---|
| *A61B 90/00* | (2016.01) |
| *A61B 5/055* | (2006.01) |
| *G16H 50/50* | (2018.01) |
| *G16H 30/20* | (2018.01) |
| *A61B 6/00* | (2006.01) |
| *A61N 5/10* | (2006.01) |
| *A61B 34/10* | (2016.01) |
| *A61B 34/20* | (2016.01) |
| *G06T 7/33* | (2017.01) |
| *G16H 50/20* | (2018.01) |
| *A61B 5/06* | (2006.01) |
| *A61B 5/00* | (2006.01) |

(52) U.S. Cl.
CPC ............ *A61B 90/37* (2016.02); *A61N 5/1049* (2013.01); *G16H 30/20* (2018.01); *G16H 30/40* (2018.01); *G16H 50/50* (2018.01); *A61B 5/06* (2013.01); *A61B 5/70* (2013.01); *A61B 6/504* (2013.01); *A61B 6/5247* (2013.01); *A61B 34/20* (2016.02); *A61B 90/361* (2016.02); *A61B 2034/105* (2016.02); *A61B 2090/364* (2016.02); *G06T 7/33* (2017.01); *G06T 2207/10081* (2013.01); *G16H 50/20* (2018.01)

(56) References Cited

U.S. PATENT DOCUMENTS

| | | | |
|---|---|---|---|
| 2004/0138548 A1 | 7/2004 | Strommer et al. | |
| 2008/0262345 A1* | 10/2008 | Fichtinger | A61B 90/39 600/426 |
| 2009/0003523 A1* | 1/2009 | Raanes | A61B 6/4458 378/65 |
| 2011/0082366 A1 | 4/2011 | Scully et al. | |

OTHER PUBLICATIONS

Decision of grant for German Application No. 102017221720.0 dated Oct. 26, 2018.
Non-Final Office Action dated Apr. 11, 2019 in U.S. Appl. No. 16/202,405.
Notice of Allowance dated Jul. 18, 2019 in U.S. Appl. No. 16/202,405.

* cited by examiner

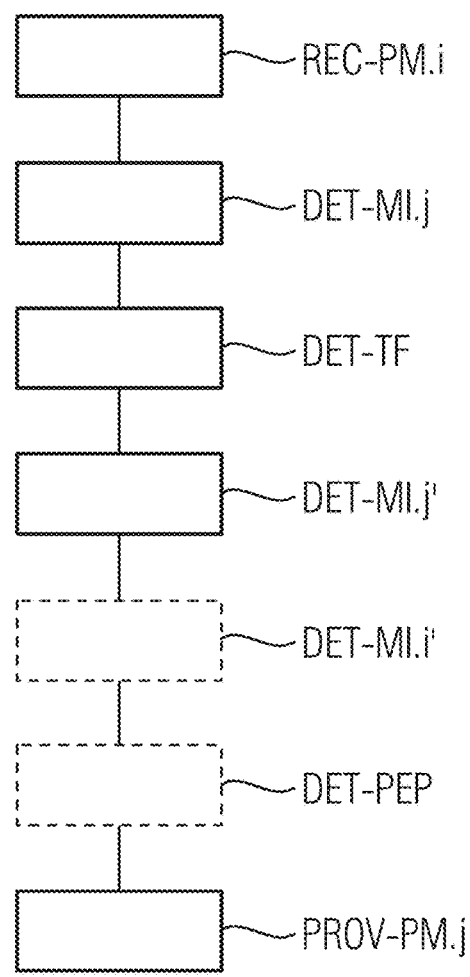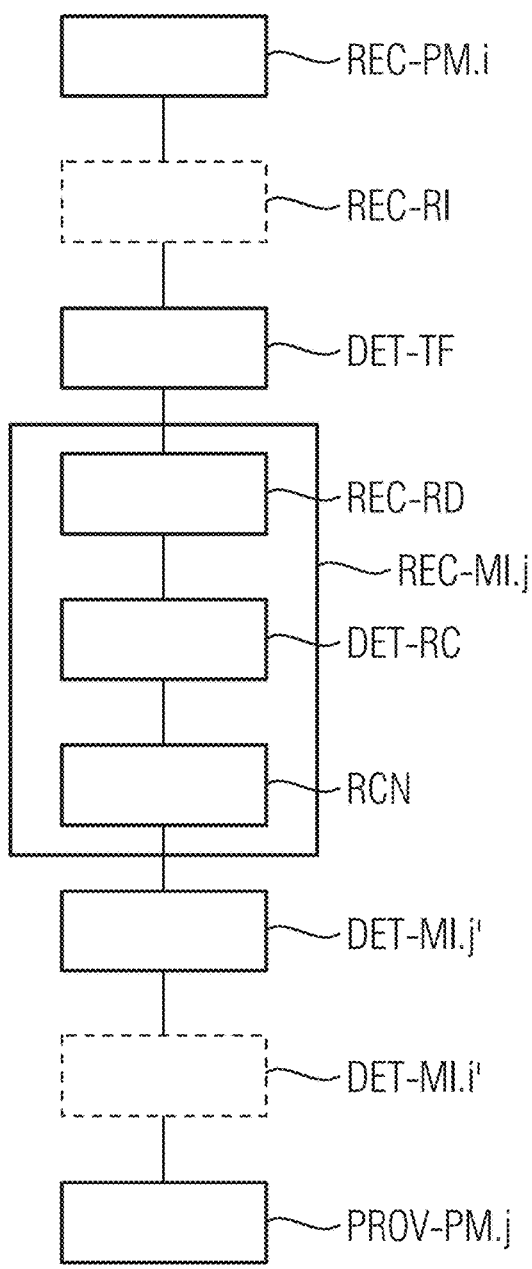

PROVIDING A PATIENT MODEL OF A PATIENT

CROSS-REFERENCE TO RELATED APPLICATIONS

The present application is a Continuation of U.S. application Ser. No. 16/202,405, filed on Nov. 28, 2018, which claims priority under 35 U.S.C. § 119 to German patent application number DE 102017221720.0, filed Dec. 1, 2017, the entire contents of each of which are incorporated herein by reference.

FIELD

Embodiments of the invention generally relate to a method, a provisioning apparatus, a medical imaging apparatus, a computer program product and a computer-readable storage medium for providing a patient model of a patient.

BACKGROUND

As a result of digitization in the health service, more data is being acquired and made available for each individual patient. However, these large datasets are distributed between different data sources in different institutions (such as hospitals, medical insurance companies or medical practices) and therefore it is not possible, or very difficult, to utilize any synergistic effects obtainable from the combination of numerous datasets.

Storage of data relating to a patient in an electronic health record ("electronic health record" is an English technical term, "EHR" for short) is known. On the one hand, an EHR is usually only a collection of data items that are difficult or impossible to link with another. On the other hand, an electronic health record of this kind has to be stored synchronously by different institutions while observing data protection.

SUMMARY

At least one embodiment of the present invention provides a patient model containing better and more accurate information on a patient.

Embodiments of the present invention are directed to a method, a provisioning apparatus, a medical imaging apparatus, a computer program product and a computer-readable storage medium.

Features, advantages or alternative embodiments mentioned herein can also be transferred to the other claimed subject matter and vice versa. In other words, the substantive claims (which are, for example, directed at an apparatus) can also be developed with the features described or claimed in connection with methods. Herein, the corresponding functional features of the methods are embodied by corresponding substantive modules.

At least one embodiment of the invention relates to a method for providing a patient model of a patient comprising the method step of receiving a first patient model of the patient via an interface, wherein the first patient model is a multi-parametric patient model, wherein the first patient model comprises a first image dataset of a patient and wherein the first image dataset is coordinated relative to a patient coordinate system. The method further comprises the method step of receiving a second image dataset of the patient via the interface, wherein the second image dataset is based on a medical imaging apparatus, wherein the second image dataset is coordinated relative to a device coordinate system and wherein the device coordinate system is a coordinate system relative to the medical imaging apparatus. The method further comprises the method step of the determination of a transformation function via a calculating unit/processor/processing circuitry, wherein the transformation function transfers the device coordinate system into the patient coordinate system. The method further comprises the method step of determining a transformed second image dataset based on the second image dataset and the transformation function via the calculating unit/processor/processing circuitry. The method further comprises the method step of providing a second patient model of the patient via the interface, wherein the second patient model is a multi-parametric patient model and wherein the second patient model comprises the transformed second image dataset. The method for providing a patient model is in particular a method for providing the second patient model.

At least one embodiment of the invention also relates to a providing unit for providing a patient model comprising the following units:
an interface embodied to receive a first patient model of the patient, wherein the first patient model is a multi-parametric patient model, wherein the first patient model comprises a first image dataset of a patient and wherein the first image dataset is coordinated relative to a patient coordinate system,
further embodied to receive a second image dataset of the patient, wherein the second image dataset is based on a medical imaging apparatus, wherein the second image dataset is coordinated relative to a device coordinate system, wherein the device coordinate system is a coordinate system relative to the medical imaging apparatus, further embodied to provide a second patient model of the patient, wherein the second patient model is a multi-parametric patient model and wherein the second patient model comprises a transformed second image dataset,
a calculating unit/processor/processing circuitry embodied to determine a transformation function, wherein the transformation function transfers the device coordinate system into the patient coordinate system, further embodied to determine the transformed second image dataset based on the second image dataset and the transformation function.

At least one embodiment of the invention also relates to a medical imaging apparatus, comprising a providing unit. The medical imaging apparatus is in particular embodied to record a second image dataset. The medical imaging apparatus can in particular be a computed tomography system, a magnetic resonance tomography system, a positron-emission tomography system, a C-arm X-ray device or an ultrasound device. The medical imaging apparatus can in particular also comprise a 3D camera embodied to record three-dimensional optical image datasets.

At least one embodiment of the invention also relates to a computer program product with a computer program and a computer-readable medium. An extensively software-based implementation has the advantage that it is also possible to retrofit a providing unit that has already been used by way of a software update in order to work in the manner according to the invention. In addition to the computer program, a computer program product of this kind can optionally comprise additional parts such as, for example, documentation and/or additional components, and hardware components, such as, for example, hardware keys (dongles etc.) for using the software.

At least one embodiment of the invention can also relate to a method for reconstructing an image dataset comprising the following method steps:

receiving a first patient model of the patient via an interface, wherein the first patient model is a multi-parametric patient model, wherein the first patient model comprises a first image dataset of a patient, wherein the first image dataset is coordinated relative to a patient coordinate system, determination of a transformation function via a calculating unit/processor/processing circuitry, wherein the transformation function transfers a device coordinate system of a medical imaging apparatus into the patient coordinate system, receiving raw data via the interface, wherein the raw data is based on an examination of the patient via the medical imaging apparatus, determining a reconstruction constraint based on the first patient model, in particular based on the first image dataset, via the calculating unit/processor/processing circuitry and reconstructing a second image dataset based on the raw data and based on the reconstruction constraint via the calculating unit/processor/processing circuitry.

At least one embodiment of the invention can also relate to a reconstruction unit comprising the following units:

an interface embodied to receive a first patient model of the patient, wherein the first patient model is a multi-parametric patient model, wherein the first patient model comprises a first image dataset of a patient, wherein the first image dataset is coordinated relative to a patient coordinate system, further embodied to receive raw data, wherein the raw data is based on an examination of the patient via a medical imaging apparatus, a calculating unit/processor/processing circuitry embodied to determine a transformation function, wherein the transformation function transfers a device coordinate system of the medical imaging apparatus into the patient coordinate system, further embodied to determine a reconstruction constraint based on the first patient model, in particular based on the first image dataset, further embodied to reconstruct the second image dataset based on the raw data and based on the reconstruction constraint via the calculating unit/processor/processing circuitry.

The method for reconstructing an image dataset or the steps thereof and the reconstruction unit or the units thereof can also implement the advantageous developments of embodiments described in connection with the method for providing a patient model and/or in connection with the providing unit for providing a patient model.

At least one embodiment of the invention can also relate to a medical imaging apparatus embodied to reconstruct an image dataset, comprising a reconstruction unit.

At least one embodiment of the invention can also relate to a computer program product with a computer program, which can be loaded directly into a memory of a reconstruction unit, with program sections for carrying out all the steps of embodiments of the method for reconstructing an image dataset when the program sections are executed by the reconstruction unit.

At least one embodiment of the invention can also relate to a computer-readable storage medium on which program sections which can be read and executed by a reconstruction unit are stored in order to carry out all the steps of embodiments of the method for reconstructing an image dataset when the program sections are executed by the reconstruction unit.

At least one embodiment of the invention can also relate to a method for providing a patient-specific image-recording parameter comprising the following method steps:

receiving a first patient model of the patient via an interface, wherein the first patient model is a multi-parametric patient model, wherein the first patient model comprises a first image dataset of a patient, wherein the first image dataset is coordinated relative to a patient coordinate system, determining the patient-specific image-recording parameter based on the first image dataset via the calculating unit/processor/processing circuitry, providing the patient-specific image-recording parameter via the interface.

At least one embodiment of the invention can also relate to a providing unit for providing a patient-specific image-recording parameter comprising the following units:

an interface embodied to receive a first patient model of the patient, wherein the first patient model is a multi-parametric patient model, wherein the first patient model comprises a first image dataset of a patient, wherein the first image dataset is coordinated relative to a patient coordinate system, further embodied to provide a patient-specific image-recording parameter, calculating unit/processor/processing circuitry embodied to determine a patient-specific image-recording parameter based on the first image dataset.

At least one embodiment of the method for providing a patient-specific image-recording parameter or the steps thereof and the providing unit for providing a patient-specific image-recording parameter or the units thereof can also implement the advantageous developments of embodiments described in connection with the method for providing a patient model and/or in connection with the providing unit for providing a patient model.

At least one embodiment of the invention can also relate to a computer program product with a computer program, which can be loaded directly into a memory of a providing unit, with program sections for carrying out all the steps of embodiments of the method for providing a patient-specific image-recording parameter when the program sections are executed by the providing unit.

At least one embodiment of the invention can also relate to a computer-readable storage medium on which program sections which can be read and executed by a providing unit are stored in order to carry out all the steps of embodiments of the method for providing a patient-specific image-recording parameter when the program sections are executed by the providing unit.

BRIEF DESCRIPTION OF THE DRAWINGS

The following describes and explains embodiments of the invention in more detail with reference to drawings.

FIG. 1 shows a first example embodiment of a method for providing a patient model, FIG. 2 shows a second example embodiment of a method for providing a patient model.

DETAILED DESCRIPTION OF THE EXAMPLE EMBODIMENTS

Figure 3:
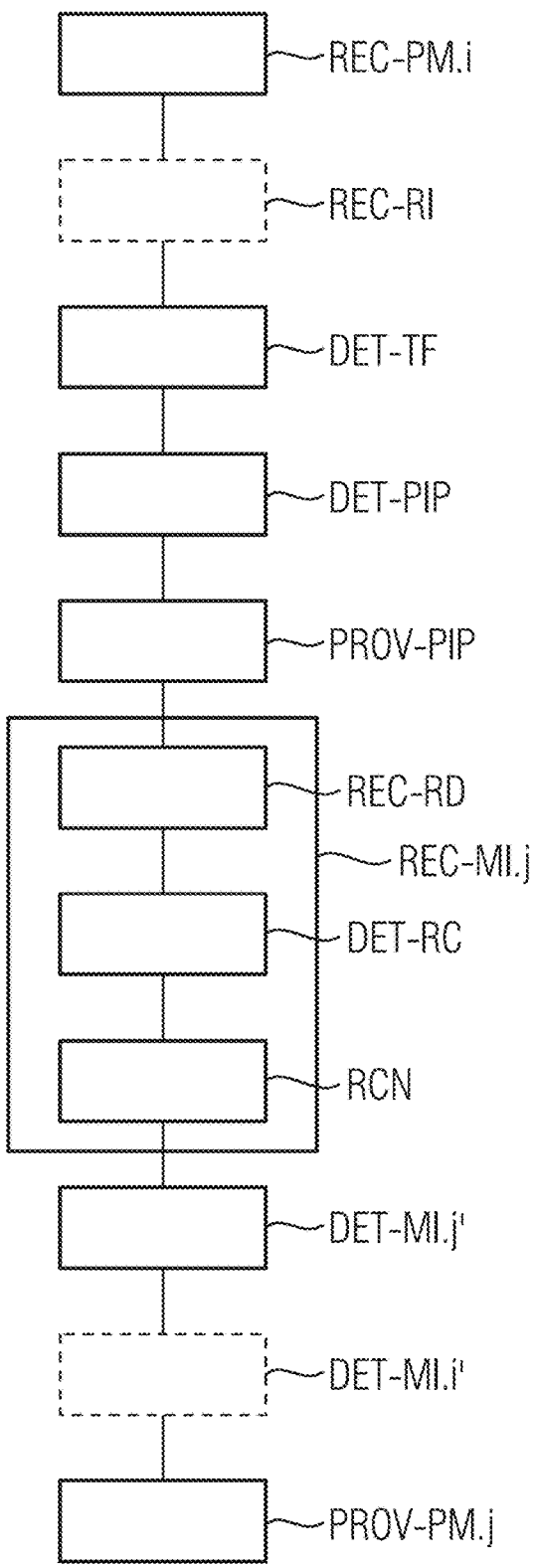
FIG. 3 shows a third example embodiment of a method for providing a patient model.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention relates to a method for providing a patient model of a patient comprising the method step of receiving a first patient model of the patient via an interface, wherein the first patient model is a multi-parametric patient model, wherein the first patient model comprises a first image dataset of a patient and wherein the first image dataset is coordinated relative to a patient coordinate system. The method further comprises the method step of receiving a second image dataset of the patient via the interface, wherein the second image dataset is based on a medical imaging apparatus, wherein the second image dataset is coordinated relative to a device coordinate system and wherein the device coordinate system is a coordinate system relative to the medical imaging apparatus. The method further comprises the method step of the determination of a transformation function via a calculating unit/processor/processing circuitry, wherein the transformation function transfers the device coordinate system into the patient coordinate system. The method further comprises the method step of determining a transformed second image dataset based on the second image dataset and the transformation function via the calculating unit/processor/processing circuitry. The method further comprises the method step of providing a second patient model of the patient via the interface, wherein the second patient model is a multi-parametric patient model and wherein the second patient model comprises the transformed second image dataset. The method for providing a patient model is in particular a method for providing the second patient model.

The inventor has recognized that the second patient model provided can improve diagnosis and/or therapy of the patient since the necessary items of information are provided in the same coordinate system and can therefore be evaluated in correlation. This in particular enables diagnosis and/or therapy to be based on two different types of image data (for example, from computed tomography and magnetic resonance tomography) or based on image data from different points in time and hence to improve diagnosis and/or therapy.

According to a further embodiment of the invention, the method further comprises the method step of determining a modified first image dataset based on the first image dataset and the transformed second image dataset via the calculating unit/processor/processing circuitry; wherein the second patient model comprises the modified first image dataset. Herein, the first image dataset was recorded at a first point in time and the second image dataset was recorded at a second point in time, wherein the second point in time is in particular a time after the first point in time.

The inventor has recognized that changes to the anatomy of the patient can occur, in particular if a large amount of time (of an order of magnitude of months or years) has passed between the first point in time and the second point in time. For example, the BMI ("body mass index" in English, "Körpermassenindex" in German) can change, in addition, there can be a build-up or loss of muscle tissue, in addition the anatomy can also change as the result of an external factor, for example an accident or operation. The determination of a modified first image dataset enables the first image dataset to be adapted to the current anatomy of the patient based on the transformed second image dataset, in particular this also enables the information in the first image dataset to be used for more accurate and better diagnosis and/or therapy.

According to a further embodiment of the invention, the step of determining the modified first image dataset is based on segmentation of the first image dataset and segmentation of the transformed second image dataset. Segmentation can in particular be segmentation of bone structures, in addition it can also in particular be segmentation of vascular structures. The inventor has recognized that the modified first image dataset can be ascertained very accurately based on segmentation since it enables account to be taken of changes to individual (segmented) structures of patient anatomy.

According to a further embodiment of the invention, the transformation function is based on a comparison of the first image dataset with the second image dataset. In other words, the transformation function is ascertained by registration of the first image dataset and the second image dataset. The transformation function in particular transfers coordinates relative to the device coordinate system into coordinates relative to the patient coordinate system, in particular, the transformation function is an invertible function, in particular an affine function. The inventor has recognized that a transformation function can be determined particularly accurately based on a comparison of the image datasets.

According to a further embodiment of the invention, the method further comprises the method step of receiving a registration image with the interface; wherein the transformation function is based on the registration image. The inventor has recognized that the transformation function can be ascertained based on a registration image without the second image dataset being present.

In particular, the second image dataset can then be ascertained based on the first image dataset and at the same time based on the second transformation function. This can enable the transformed second image dataset or the second image dataset to be ascertained more quickly and/or more accurately. In addition, as a rule, a registration image contains less information than the second image dataset (for example, the registration image can be of a lower dimension than the second image dataset) and therefore the transformation function can be calculated particularly quickly and efficiently.

According to a further embodiment of the invention, the registration image is a three-dimensional optical image of the patient, wherein the three-dimensional optical image was recorded with an optical image recording unit, wherein the optical image recording unit is arranged on the medical imaging apparatus. The optical image recording unit is in particular an optical 3D camera. The inventor has recognized that a three-dimensional optical image enables a particularly accurate determination of the transformation function before the recording of the second image dataset and, at the same time, unlike recording by way of ionizing radiation, an optical three-dimensional image does not expose the patient to additional radiation and, unlike recording by way of magnetic resonance tomography, an optical three-dimensional image does not result in any additional heating of patient tissue. In particular, the use of a three-dimensional optical-registration image makes it possible completely to dispense with the recording of a scout view via the medical imaging apparatus and the exposure to radiation or heat associated therewith when the planning of the medical imaging examination is based on the first patient model. In particular, a three-dimensional optical-registration image can also be recorded more quickly than a scout view of the medical imaging apparatus thus enabling the overall duration of the medical imaging examination to be reduced.

According to a further embodiment of the invention, the method further comprises the method step of determining a patient-specific image-recording parameter based on the first image dataset via the calculating unit/processor/processing circuitry, in addition the method comprises the method step of providing the patient-specific image-recording parameter via the interface. Alternatively, the patient-specific image-recording parameter can be calculated based on the first patient model. The patient-specific image-recording parameter is in particular a parameter relating to the recording of the second image dataset via the medical imaging apparatus. A patient-specific image-recording parameter can in particular be determined by adapting a prespecified image-recording parameter or a prespecified patient-specific image-recording parameter.

According to a further possible embodiment of the invention, imaging via the medical imaging apparatus is based on the patient-specific image-recording parameter when the second image dataset is recorded via the medical imaging apparatus. The inventor has recognized that an image-recording parameter is possible in a particularly efficient manner and in particular without preparatory preliminary recordings, possibly entailing exposure to radiation heat, based on the first image dataset or based on the first patient model. For example, an image-recording parameter can be determined such that prespecified limit values for the exposure of patient tissue to radiation or heat are not exceeded. In addition, this enables the patient positioning to be determined.

According to a further embodiment of the invention, the step of receiving the second image dataset is performed after, in particular after in terms of time, the step of determining the transformation function. In addition, the step of receiving the second image dataset comprises the substep of receiving raw data via the interface, wherein the raw data is based on an examination of the patient via the medical imaging apparatus; the substep of determining a reconstruction constraint based on the first patient model, in particular based on the first image dataset, via the calculating unit/processor/processing circuitry; and the substep of the reconstruction of the second image dataset based on the raw data and based on the reconstruction constraint via the calculating unit/processor/processing circuitry.

The inventor has recognized that this advantageous development enables the second image dataset to be reconstructed particularly quickly and efficiently since reconstruction constraints are available as additional information in addition to the raw data and reconstruction does not have to be performed exclusively based on the raw data. In addition, the amount of raw data required can be reduced based on a reconstruction constraint, for example by compressed detection (English technical terms are "compressed sensing", "compressive sampling" or "sparse sampling"); this reduction enables the duration of the actual image recording to be reduced.

According to a further embodiment of the invention, the first image dataset is a template-image dataset, wherein the template-image dataset is selected based on a patient parameter of the patient. According to a further possible embodiment of the invention, the patient parameter relates to at least one of the following parameters: the patient's age, the patient's gender, the patient's height, the patient's weight. According to a further possible embodiment of the invention, the template dataset is furthermore based on the patient parameter. The inventor has recognized that, in particular on first contact with the patient, a large amount of information on the patient is already available based on a template-image dataset selected specifically for the patient and this information does not then have to be ascertained by diagnostic methods (for example an imaging examination of the entire patient). Therefore, it is possible to initialize a patient model quickly and inexpensively by way of a template-image dataset. In this case, therefore, the first patient model in particular comprises the template-image dataset. In particular, during the initialization, the first patient model can comprise further template-image datasets, wherein the template-image datasets relate to different parameters (for example Hounsfield units and segmentation of the body into different organs).

According to a further embodiment of the invention, the patient parameter is a three-dimensional optical image of the patient, in addition, the template-image dataset is adapted based on the three-dimensional optical image of the patient. The inventor has recognized that adaptation of the template-image dataset based on the three-dimensional optical image enables the template-image dataset to be adapted particularly accurately to the actual anatomy of the patient.

According to a further embodiment of the invention, the method further comprises the method step of determining a second patient-specific exposure parameter based on the transformed second image dataset via the calculating unit/processor/processing circuitry. A patient-specific exposure parameter can in particular be a patient-specific dose parameter and/or a patient-specific heat parameter. Alternatively, the patient-specific exposure parameter can also relate to exposure to contrast medium. According to a further possible embodiment of the invention the second patient model comprises the second patient-specific exposure parameter. The second patient-specific exposure parameter can in particular be a second organ-specific exposure parameter. The inventor has recognized that the second patient-specific exposure parameter can provide information on the local exposure of the patient to, for example, ionizing radiation (in the case of a patient-specific dose parameter, for example as a result of examinations using computed tomography or positron emission tomography or of medical irradiation), heat or contrast medium during a medical imaging examination. Herein, the heating of tissue due to a magnetic resonance tomography examination is caused by the irradiation of radio-frequency radiation (frequency between 60 MHz and 120 MHz). This information can in particular be relevant for follow-up examinations in order to comply with a time-related limit value for patient exposure.

According to a further possible embodiment of the invention, the first patient model also comprises a first patient-specific exposure parameter, wherein the second patient-specific exposure parameter is also based on the first patient-specific exposure parameter. The inventors have recognized that such a dependence enables the second patient-specific exposure parameter to be used as a cumulative exposure parameter over a plurality of examinations and hence to provide better information for any possible follow-up examinations.

According to a further embodiment of the invention, the second patient model comprises a hash value of the first patient model. The inventor has recognized that use of hash values of this kind of makes a subsequent change to the first patient model no longer possible, in particular this can achieve a revision-proof storage of the patient models. Herein, revision-proof storage of data is in particular necessary in the field of medical information, and herein in particular for electronic health records.

According to a further embodiment of the invention, the method further comprises the method step of storing the first patient model and the second patient model as sequential blocks in a block-chain database via a storage unit. The inventors have recognized that storage in a block-chain database enables the implementation of a distributed and at the same time revision-proof database of patient models. In particular, therefore, a plurality of medical institutions can provide patient models of patients that are in each case based on information from other institutions.

According to a further possible embodiment of the invention, the method further comprises the method step of superimposing the second image dataset with the first image dataset via an output unit. The inventor has recognized that a superimposed display enables the second image dataset to be displayed in a larger anatomical context of the first image dataset even when the second image dataset is restricted to only a part of the anatomy of the patient (for example to keep the exposure of the patient or the duration of the medical imaging examination short). This enables the second image dataset to be interpreted in an anatomical context and hence better and more accurately.

According to a further possible embodiment of the invention, the method further comprises the method step of the creation of a three-dimensional prosthesis based on the first patient model or based on the second patient model via a three-dimensional printing unit. A three-dimensional printing unit is in particular a 3D printer. The inventors have recognized that, based on the first or the second patient model, a prosthesis can be adapted particularly accurately and specifically to the patient. Herein, a prosthesis can in particular be a vascular prosthesis or a joint prosthesis, the prosthesis material can in particular be plastic or metal. In particular the method of selective laser sintering is known for the three-dimensional creation of a prosthesis from metal.

According to a further possible embodiment of the invention, the method further comprises the method step of receiving patient information for the patient via the interface; and the method step of the adaptation of the second patient model based on the patient information. The patient information can in particular be diagnostic or therapeutic information, for example an operation report (for example, relating to the implantation of a prosthesis, the transplantation of tissue or the removal of parts of the human body). During the adaptation of the second patient model, it is in particular possible for the transformed second image dataset and/or the modified first image dataset to be adapted. The inventor has recognized that, based on the patient information, changes to the anatomy of the patient can be acquired very efficiently and, as a result, the second patient model is a particularly good reproduction of the anatomy of the patient.

At least one embodiment of the invention also relates to a providing unit for providing a patient model comprising the following units:

an interface embodied to receive a first patient model of the patient, wherein the first patient model is a multi-parametric patient model, wherein the first patient model comprises a first image dataset of a patient and wherein the first image dataset is coordinated relative to a patient coordinate system, further embodied to receive a second image dataset of the patient, wherein the second image dataset is based on a medical imaging apparatus, wherein the second image dataset is coordinated relative to a device coordinate system, wherein the device coordinate system is a coordinate system relative to the medical imaging apparatus, further embodied to provide a second patient model of the patient, wherein the second patient model is a multi-parametric patient model and wherein the second patient model comprises a transformed second image dataset, a calculating unit/processor/processing circuitry embodied to determine a transformation function, wherein the transformation function transfers the device coordinate system into the patient coordinate system, further embodied to determine the transformed second image dataset based on the second image dataset and the transformation function.

Such a providing unit can in particular be embodied to carry out the embodiments of the above-described methods according to the invention and the aspects thereof. The providing unit is embodied to carry out these methods and the aspects and embodiments thereof in that the interface and the calculating unit/processor/processing circuitry are embodied to carry out the corresponding method steps.

At least one embodiment of the invention also relates to a medical imaging apparatus, comprising a providing unit. The medical imaging apparatus is in particular embodied to record a second image dataset. The medical imaging apparatus can in particular be a computed tomography system, a magnetic resonance tomography system, a positron-emission tomography system, a C-arm X-ray device or an ultrasound device. The medical imaging apparatus can in particular also comprise a 3D camera embodied to record three-dimensional optical image datasets.

At least one embodiment of the invention also relates to a computer program product with a computer program and a computer-readable medium. An extensively software-based implementation has the advantage that it is also possible to retrofit a providing unit that has already been used by way of a software update in order to work in the manner according to the invention. In addition to the computer program, a computer program product of this kind can optionally comprise additional parts such as, for example, documentation and/or additional components, and hardware components, such as, for example, hardware keys (dongles etc.) for using the software.

At least one embodiment of the invention can also relate to a method for reconstructing an image dataset comprising the following method steps:

receiving a first patient model of the patient via an interface,
wherein the first patient model is a multi-parametric patient model,
wherein the first patient model comprises a first image dataset of a patient,
wherein the first image dataset is coordinated relative to a patient coordinate system, determination of a transformation function via a calculating unit/processor/processing circuitry, wherein the transformation function transfers a device coordinate system of a medical imaging apparatus into the patient coordinate system, receiving raw data via the interface, wherein the raw data is based on an examination of the patient via the medical imaging apparatus, determining a reconstruction constraint based on the first patient model, in particular based on the first image dataset, via the calculating unit/processor/processing circuitry and reconstructing a second image dataset based on the raw data and based on the reconstruction constraint via the calculating unit/processor/processing circuitry.

The method for reconstructing an image dataset is in particular a method for reconstructing the second image dataset The inventor has recognized that the reconstruction of an image dataset, in particular a tomographic image dataset, can be performed much more quickly and efficiently based on information (or reconstruction constraints) on a patient made available by a patient model. In addition, the amount of raw data required can be reduced based on a reconstruction constraint, for example by compressed detection (English technical terms are "compressed sensing", "compressive sampling" or "sparse sampling"); this reduction enables the duration of the actual image recording to be reduced.

According to a further embodiment of the invention, the method for reconstructing an image dataset also comprises the method step of determining a patient-specific image-recording parameter based on the first image dataset via the calculating unit/processor/processing circuitry, the method also comprises the method step of providing the patient-specific image-recording parameter via the interface. Alternatively, the patient-specific image-recording parameter can be calculated based on the first patient model. The patient-specific image-recording parameter is in particular a parameter relating to the recording of the second image dataset via the medical imaging apparatus. A patient-specific image-recording parameter can in particular be determined by the adaptation of a prespecified image-recording parameter or a prespecified patient-specific image-recording parameter. According to a further possible embodiment of the invention, imaging via the medical imaging apparatus is based on the patient-specific image-recording parameter when the second image dataset is recorded via the medical imaging apparatus.

At least one embodiment of the invention can also relate to a reconstruction unit comprising the following units:

an interface embodied to receive a first patient model of the patient, wherein the first patient model is a multi-parametric patient model, wherein the first patient model comprises a first image dataset of a patient, wherein the first image dataset is coordinated relative to a patient coordinate system, further embodied to receive raw data, wherein the raw data is based on an examination of the patient via a medical imaging apparatus, a calculating unit/processor/processing circuitry embodied to determine a transformation function, wherein the transformation function transfers a device coordinate system of the medical imaging apparatus into the patient coordinate system, further embodied to determine a reconstruction constraint based on the first patient model, in particular based on the first image dataset, further embodied to reconstruct the second image dataset based on the raw data and based on the reconstruction constraint via the calculating unit/processor/processing circuitry.

The method for reconstructing an image dataset or the steps thereof and the reconstruction unit or the units thereof can also implement the advantageous developments of embodiments described in connection with the method for providing a patient model and/or in connection with the providing unit for providing a patient model.

At least one embodiment of the invention can also relate to a medical imaging apparatus embodied to reconstruct an image dataset, comprising a reconstruction unit.

At least one embodiment of the invention can also relate to a computer program product with a computer program, which can be loaded directly into a memory of a reconstruction unit, with program sections for carrying out all the steps of embodiments of the method for reconstructing an image dataset when the program sections are executed by the reconstruction unit.

At least one embodiment of the invention can also relate to a computer-readable storage medium on which program sections which can be read and executed by a reconstruction unit are stored in order to carry out all the steps of embodiments of the method for reconstructing an image dataset when the program sections are executed by the reconstruction unit.

At least one embodiment of the invention can also relate to a method for providing a patient-specific image-recording parameter comprising the following method steps:
- receiving a first patient model of the patient via an interface,
- wherein the first patient model is a multi-parametric patient model,
- wherein the first patient model comprises a first image dataset of a patient,
- wherein the first image dataset is coordinated relative to a patient coordinate system,
  - determining the patient-specific image-recording parameter based on the first image dataset via the calculating unit/processor/processing circuitry,
  - providing the patient-specific image-recording parameter via the interface.

The inventor has recognized that an image-recording parameter can be provided specifically for a patient based on a patient model. This image-recording parameter can then be used to perform medical imaging of the patient that is more accurate and better adapted to the patient anatomy.

At least one embodiment of the invention can also relate to a providing unit for providing a patient-specific image-recording parameter comprising the following units:
- an interface embodied to receive a first patient model of the patient, wherein the first patient model is a multi-parametric patient model, wherein the first patient model comprises a first image dataset of a patient, wherein the first image dataset is coordinated relative to a patient coordinate system,
- further embodied to provide a patient-specific image-recording parameter,
- calculating unit/processor/processing circuitry embodied to determine a patient-specific image-recording parameter based on the first image dataset.

At least one embodiment of the method for providing a patient-specific image-recording parameter or the steps thereof and the providing unit for providing a patient-specific image-recording parameter or the units thereof can also implement the advantageous developments of embodiments described in connection with the method for providing a patient model and/or in connection with the providing unit for providing a patient model.

At least one embodiment of the invention can also relate to a computer program product with a computer program, which can be loaded directly into a memory of a providing unit, with program sections for carrying out all the steps of embodiments of the method for providing a patient-specific image-recording parameter when the program sections are executed by the providing unit.

At least one embodiment of the invention can also relate to a computer-readable storage medium on which program sections which can be read and executed by a providing unit are stored in order to carry out all the steps of embodiments of the method for providing a patient-specific image-recording parameter when the program sections are executed by the providing unit.

A patient model of a patient comprises one or more image datasets of the patient. In addition, a patient model can comprise further medical data relating to the patient (for example laboratory data, operation reports, diagnoses) or personal data (for example name, age, gender, height, weight). A patient model can be assigned a point in time, in particular a point in time corresponding to the creation of the patient model (another word for this point in time is "time stamp"). If the first patient model is assigned a first point in time and the second patient model is assigned a second point in time, the second point in time is in particular a time after the first point in time.

An image dataset relative to a coordinate system is a mapping of coordinates relative to the coordinate system for a parameter space; herein coordinate tuples are depicted on one parameter in each case. Herein, a parameter can be a discrete parameter, in particular binary, or an element of a prespecified discrete set. However, a parameter can also be a continuous parameter, in particular a rational or real number. However, a parameter can also comprise a plurality of discrete and/or continuous parameters. In particular, the parameter can also relate to one or more intensity values. The coordinates or coordinate tuples can also be discrete or continuous. In the case of discrete coordinates, an image dataset can in particular assign one parameter in each case to pixels or voxels.

An image dataset can in particular be a two-dimensional, three-dimensional or four-dimensional image dataset. An n-dimensional image dataset relative to an at least n-dimensional coordinate system is a mapping of n-dimensional coordinates relative to the at least n-dimensional coordinate system for a parameter space; herein, n-dimensional coordinate tuples are depicted on one parameter in each case. A dimension is in particular a spatial dimension or a temporal dimension.

A first image dataset is in particular a first medical image dataset, a second image dataset is in particular a second medical image dataset. A medical image dataset is in particular an image dataset of a patient for the purpose of the diagnosis and/or therapy of this patient. A medical image dataset is in particular an X-ray image dataset, a computed tomography image dataset, a magnetic-resonance tomography image dataset, a positron-emission tomography image dataset, an ultrasound image dataset or an optical image dataset, in particular an optical three-dimensional image dataset of the patient. The type of the first image dataset and the second image dataset can be identical, the type of the first image dataset can also differ from the type of the second image dataset. A medical image dataset can also be recorded using a contrast medium in the patient.

The image region of an image dataset is in particular the volume depicted by the image dataset or the area depicted by the image dataset. The image region of the first image dataset can in particular overlap the image region of the second image dataset. In particular, it is also possible for the image region of the first image dataset to be identical to the image region of the second image dataset.

A transformation function is in particular an invertible function that maps a patient-coordinate system on a device coordinate system or vice versa. In particular, the transformation function is an affine transformation. The transformation function can in particular also transfer the patient coordinate system into the device coordinate system, in particular, the transformation function can also be a bijective function.

A patient-specific image-recording parameter is in particular a parameter of a medical imaging examination that is prespecified for the imaging of the patient via the medical imaging apparatus and/or influences imaging of the patient by way of a medical imaging examination. In particular, the patient-specific image-recording parameter can also be a parameter of the medical imaging apparatus. A patient-specific exposure parameter in particular relates to stress on the patient from a medical imaging examination, for example from a radiation dose, heat, contrast medium or other effects exerting an influence on the body of the patient.

FIG. 1 shows a first example embodiment of a method for providing a patient model PM.i, PM.j, PM.k of a patient P.

In this and in the following example embodiments, the methods are described with respect to the first patient model PM.i, the second patient model PM.j, the first image dataset MI.i and the second image dataset MI.j. It is also possible to describe the methods with respect to the first patient model PM.j, the second patient model PM.k, the first image dataset MI.j and the second image dataset MI.k. Generally, the embodiments described can generate a concatenation of sequential patient models by way of multiple application.

The first step of the first example embodiment depicted of a method for providing a patient model PM.i, PM.j, PM.k is the reception REC-PM.i of a first patient model PM.i of the patient P via an interface PU.i.IF, PU.j.IF, wherein the first patient model PM.i is a multi-parametric patient model, wherein the first patient model PM.i comprises a first image dataset MI.i of a patient P, wherein the first image dataset MI.i is coordinated relative to a patient coordinate system PCS.

In this example embodiment, the first patient model PM.i is a mapping of three-dimensional coordinates relative to the patient coordinate system on a multidimensional (here n-dimensional) result set:

$$PM.i: R^3 \to M_1 \times \ldots \times M_n;$$

$$\begin{pmatrix} x_1 \\ x_2 \\ x_3 \end{pmatrix} \mapsto \begin{pmatrix} f^{(1)}(x_1, x_2, x_3) \\ \vdots \\ f^{(n)}(x_1, x_2, x_3) \end{pmatrix}$$

Alternatively, the first patient model PM.i can be a mapping of three-dimensional voxels (coordinatized by a three-dimensional index set I1×I2×I3) on a multidimensional (here n-dimensional) result set:

$$PM.i: I_1 \times I_2 \times I_3 \to M_1 \times \ldots \times M_n;$$

$$\begin{pmatrix} i \\ j \\ k \end{pmatrix} \mapsto \begin{pmatrix} f^{(1)}_{ijk} \\ \vdots \\ f^{(n)}_{ijk} \end{pmatrix}$$

The first patient model PM.i is therefore in particular defined by its components $f^{(1)}, \ldots, f^{(n)}$, each individual component can in turn be interpreted as a mapping:

$$f^{(m)}: R^3 \to M_m;$$

$$\begin{pmatrix} x_1 \\ x_2 \\ x_3 \end{pmatrix} \mapsto f^{(m)}(x_1, x_2, x_3)$$

$$f^{(m)}: I_1 \times I_2 \times I_3 \to M_m;$$

$$\begin{pmatrix} i \\ j \\ k \end{pmatrix} \mapsto f^{(m)}_{ijk}$$

The constituents $M_1, \ldots, M_n$ of the result set and their associated components $f^{(1)}, \ldots, f^{(n)}$ can map different patient-specific parameters. For example, here, $f^{(1)}$ corresponds to the first image dataset MI.i, which, in the example embodiment depicted, is a computed tomography image dataset. In particular, $f^{(1)}(x_1,x_2,x_3)$ or $f^{(1)}_{ijk}$ then corresponds to a Hounsfield value in HU ("Hounsfield units", a German technical term is "Hounsfieldeinheiten"), which is assigned to the patient by the first image dataset MI.i in the coordinate $(x_1,x_2,x_3)$ or in the voxel with the indices (i,j,k). Herein, the Hounsfield value corresponds to X-ray attenuation in a tissue relative to attenuation in water multiplied by 1000 HU.

The first component $f^{(1)}$ or the remaining components $f^{(2)}, \ldots, f^{(n)}$ can also correspond to other parameters. This can entail other image datasets, for example a magnetic-resonance image dataset, an X-ray fluoroscopy image dataset or an optical image dataset, in particular a three-dimensional optical image dataset. The first component $f^{(1)}$ or the remaining components $f^{(2)}, \ldots, f^{(n)}$ can also be segmentations of image datasets, for example segmentations of bones and/or specific organs. Alternatively, it is also possible for fatty regions or muscle regions of the patient to be segmented, again alternatively, nerve bundles can be segmented (for example based on magnetic resonance tomography with a sequence matched to such a distinction), again alternatively, it is possible for blood vessels to be segmented (for example based on medical imaging with contrast media). Herein, segmentation can be performed automatically, semi-automatically or manually, in particular, a radiologist can use manual segmentation to define regions of interest, for example regions with a tumor. In the case of segmentation, the associated constituent M of the result set can in particular be the amount M={0,1}, wherein a coordinate or a voxel is assigned the value 1 when the body part to be segmented is located on this coordinate or on this voxel and wherein a coordinate or a voxel is assigned the value 0 when the body part to be segmented is not located on this coordinate or on this voxel. The first component $f^{(1)}$ or the remaining components $f^{(2)}, \ldots, f^{(n)}$ can also depict further three-dimensional information, for example a prosthesis introduced artificially in or on the patient, wherein here again the value 1 is assigned to a coordinate or a voxel, when the prosthesis is located on this coordinate or on this voxel and wherein the value 0 is assigned to a coordinate or a voxel when the prosthesis is not located on this coordinate or on this voxel. If the prosthesis is made of various different materials, it is also possible to use values other than the values 0 and 1. Examples of such prostheses are joint prostheses, vascular prostheses, cardiac pacemakers, defibrillators, screws and metal plates.

The first component $f^{(1)}$ or the remaining components $f^{(2)}, \ldots, f^{(n)}$ can also correspond to other low-dimensional parameters. For example, one of the components $f^{(m)}$ can correspond to a two-dimensional X-ray projection along a direction vector $v=(v_1, v_2, v_3)$. This two-dimensional X-ray projection can, for example, be stored such that only $f^{(m)}(x_1, x_2, 0)$ or $f^{(m)}_{ijk}$ take on values different from 0 and so that the direction vector v is stored at the same time. Alternatively, it is also possible for the two-dimensional X-ray projection to be stored such that $f^{(m)}(x_1, x_2, x_3)=f^{(m)}(x_1+\lambda v_1, x_2+\lambda v_2, \lambda_3+\lambda v_3)$ or $f^{(m)}_{ijk}=f^{(m)}_{(i+\lambda v1)(j+\lambda v2)(k+\lambda v3)}$ for a real or integer $\lambda$.

The first component $f^{(1)}$ or the remaining components $f^{(2)}, \ldots, f^{(n)}$ can also correspond to other zero-dimensional parameters, in other words scalar parameters. Examples of such scalar parameters are the weight, height, age and gender of the patient. In addition, it is also possible to store diagnoses in this format. Alternatively, such zero-dimensional parameters can also be stored as metadata in the first patient model PM.i.

If, in the first step depicted of the reception REC-PM.i of a first patient model PM.i of the patient P, as yet no anatomical information on the patient is available, the first patient model PM.i can in particular comprise one or more template-image datasets TMI.1, ..., TM.13 as the first image dataset MI.i, wherein the template-image datasets TMI.1, ..., TM.9 can be selected and/or adapted according to a patient parameter of the patient P. Thus it is also possible, without further anatomical information on the patient, to use a comprehensive first patient model PM.i.

The second step of the first example embodiment depicted of the method for providing a patient model PM.i, PM.j, PM.k is the reception REC-MI.j of a second image dataset MI.j of the patient via the interface PU.i.IF, PU.j.IF, wherein the second image dataset MI.j is based on a medical imaging apparatus MOD, MOD', wherein the second image dataset MI.j is coordinated relative to a device coordinate system MCS and wherein the device coordinate system MCS is a coordinate system relative to the medical imaging apparatus MOD, MOD'.

In the third example embodiment depicted, the medical imaging apparatus MOD, MOD' is a computed tomography system, and the second image dataset MI.j is a computed tomography image dataset of the patient P that was recorded via the computed tomography system. In the example embodiment depicted, the second image dataset MI.j is defined by a function $g^{(n+1)}(y_1, y_2, y_3)$, wherein $y_1, y_2$ and $y_3$ are coordinates relative to the device coordinate system MCS. Alternatively, the second image dataset MI.j can also be defined by voxel data $g^{(n+1)}_{ijk}$, wherein here the voxels are defined relative to the device coordinate system MCS. In particular, the function or the voxel data assign a Hounsfield value in HU to a coordinate tuple or a voxel.

The third step of the first example embodiment depicted of the method for providing a patient model PM.i, PM.j, PM.k is the determination DET-TF of a transformation function TF via a calculating unit PU.i.CU, PU.j.CU, such as a processor for example, wherein the transformation function TF transfers the device coordinate system MCS into the patient coordinate system PCS.

In the example embodiment depicted, the transformation function TF is determined based on the first image dataset MI.i and the second image dataset MI.j in that the second image dataset MI.j is registered with the first image dataset MI.i. Different methods for image registration are known to the person skilled in the art, it is in particular possible to differentiate between feature-based and image-value-based methods. With image-value-based methods, registration is performed directly by way of the parameters of the first image dataset MI.i and the second image dataset MI.j, with feature-based methods, first features (for example points, lines, areas or volumes) in the first image dataset MI.i and corresponding features in the second image dataset MI.j are identified and the registration is performed based on these features. Herein, the extraction of the features can be performed manually, semi-automatically or automatically. In the example embodiment depicted, the registration is based on automatic segmentation of bone regions in the first image dataset MI.i and the second image dataset MI.j. For example, first the transformation function TF is selected as the identity function that is optimized iteratively based on the difference between the bone regions in the first image dataset MI.i and the bone regions in a temporary transformed second image dataset. In this example embodiment, the transformation function TF is then an affine mapping of coordinates relative to the device coordinate system MCS on coordinates relative to the patient coordinate system PCS:

$$TF: R^3 \to R^3;$$

$$\begin{pmatrix} x_1 \\ x_2 \\ x_3 \end{pmatrix} \mapsto \begin{pmatrix} TF_1(x_1, x_2, x_3) \\ TF_2(x_1, x_2, x_3) \\ TF_3(x_1, x_2, x_3) \end{pmatrix} = \begin{pmatrix} y_1 \\ y_2 \\ y_3 \end{pmatrix}$$

In particular, the transformation function TF is a norm-sustaining mapping, i.e. a rotation or shift. Alternatively, the transformation function TF can also be a non-affine mapping of coordinates relative to the device coordinate system MCS on coordinates relative to the patient coordinate system PCS. The fourth step of the first example embodiment depicted of the method for providing a patient model PM.i, PM.j, PM.k is the determination DET-MI.j' of a transformed second image dataset MI.j' based on the second image dataset MI.j and the transformation function TF via the calculating unit/processor/processing circuitry PU.i.CU, PU.j.CU.

In the example embodiment depicted, the transformed second image dataset MI.j' is defined by a function $f^{(n+1)}(x_1, x_2, x_3)$, wherein this function is a concatenation $f^{(n+1)}=g^{(n+1)} \circ TF$ of the transformation function TF with the function corresponding to the second image dataset MI.j:

$$f^{(n+1)}: \begin{pmatrix} x_1 \\ x_2 \\ x_3 \end{pmatrix} \mapsto g^{(n+1)}(TF_1(x_1, x_2, x_3), TF_2(x_1, x_2, x_3), TF_3(x_1, x_2, x_3))$$

The fifth step of the first example embodiment depicted of the method for providing a patient model PM.i, PM.j, PM.k is the determination DET-MI.i' of a modified first image dataset MI.i' based on the first image dataset MI.i and the transformed second image dataset MI.j' via the calculating unit/processor/processing circuitry PU.i.CU, PU.j.CU. The fifth step of the determination DET-MI.i' of a modified first image dataset MI.i' is an optional step, this optional step can also be called "morphing".

In the example embodiment depicted, the determination of the transformed second image dataset MI.j' is performed by way of a transformation function TF based on registration of the first image dataset MI.i and the second image dataset MI.j, wherein registration is based on segmentation of bone regions. Herein, this transformation function TF is a linear transformation and embodied to transfer a patient-specific coordinate system PCS and a device-specific coordinate system into one another. In particular, due to its linearity, the transformation function TF is not able to detect any (non-linear) change to the patient anatomy. However, it is advantageous for the first image dataset MI.i to be modified such that it is adapted to the current patient anatomy.

If the first image dataset MI.i and the second image dataset MI.j are of the same type of image dataset (i.e. in each case a computed tomography image dataset or in each case a magnetic-resonance tomography image dataset), in order to determine DET-MI.i' of the modified first image dataset MI.i', it is only necessary to adapt this to the changed anatomy of the patient. The changed anatomy of the patient P is, for example, the result of growth processes in children and adolescents, a change in the body-mass index or changes due to muscle build-up, muscle atrophy and/or natural ageing processes. The determination of the modified first image dataset MI.i' can then be based on rules derived from general anatomical knowledge, for example knowledge of the typical location of fatty deposits in dependence on the age and gender of the patient (these are for example also depicted in FIGS. 12 and 13). Alternatively, it is also possible to use patient models PM.i, PM.j of other patients in order to determine the modified first image dataset MI.i' by way of methods for analyzing big data ("big data" is an English technical term), statistical methods or methods of artificial intelligence. Herein, it is in particular possible to use "deep learning" ("tiefes Lernen" in German) or image classifiers based on neural networks.

In an advantageous embodiment, for the determination of the modified first image dataset MI.i', the bone structures are first adapted to the changed anatomy. This is first performed with the bone structures in the image region of the transformed second image dataset MI.j' and then with the bone structures outside the image region of the transformed second image dataset MI.j'. After the bone structures, the soft-tissue structures are then adapted to the changed anatomy, for example, it is possible to include a rotation of the cardiac muscle (a technical term is myocardium) about an axis (resulting from the change of position of the diaphragm due to a change in the BMI). It is also, for example, possible to include changes to the liver due to obesity or alcohol abuse. It is also possible for the soft-tissue structures outside the image region of the transformed second image dataset MI.j' to be adapted based on empirical values to the changes in the image region of the transformed second image dataset MI.j', for example, account can be taken of a general growth rate, a general body fat parameter or the general parameter of the muscular mass.

If the first image dataset MI.i and the second image dataset MI.j were recorded with different types of medical imaging apparatuses MOD, MOD', in addition to the described adaptations to the changed patient anatomy, it is also possible for the modified first image dataset MI.i' to be determined such that the modified first image dataset MI.i' maps a larger region of the patient than the first image dataset MI.i'. In other words, therefore, the transformed second image dataset MI.j' can be used to expand the first image dataset MI.i beyond its image region. For example, it is known from magnetic resonance tomography to derive different image contrasts from the tissue relaxation parameters (for example T1 and T2). In addition, it is known to derive synthetic computed tomography values (i.e. synthetic Hounsfield units) from magnetic resonance tomography voxel values. This synthetic determination of image values is, for example, based on a correspondence table. These correspondence tables can, in a first step, be calibrated at the overlapping region of the image regions of the first image dataset MI.i and the transformed second image dataset MI.j' and advantageously also based on the segmentation of individual organs. In a second step, the correspondence table is then applied to regions outside the overlapping region in order to determine the modified first image dataset MI.i'. Advantageously, it is also possible to use patient models of other patients in order to create and/or improve the correspondence tables.

In a further advantageous embodiment, it is also possible to determine the modified first image dataset MI.i' based on diagnostic or therapeutic information. For example, it is possible to derive from an electronic health record information on anatomy-changing interventions (amputations, organ transplants, the use of cardiac pacemakers or prostheses), for example from free text with computer linguistic methods or based on second image datasets MI.j from the electronic health record.

The sixth step of the first example embodiment depicted of the method for providing a patient model PM.i, PM.j, PM.k is the determination DET-PEP of a second patient-specific exposure parameter based on the transformed second image dataset MI.j via the calculating unit/processor/processing circuitry PU.i.CU, PU.j.CU. This step is an optional step. In the example embodiment depicted, the second patient-specific exposure parameter is a patient-specific dose parameter, i.e. in particular the radiation dose absorbed by the patient due to the recording of the second image dataset MI.j, which was calculated based on the transformed second image dataset MI.j'. In particular, known from the transformed second image dataset MI.j' are the HU values in patient coordinates, based on information of the medical imaging apparatuses MOD, MOD' for image recording (for example the parameters of the individual X-ray recordings that have been combined to form a tomographic image) of the second image dataset MI.j and based on the transformation function.

Alternatively, it is also possible for the first patient model PM.i to comprise a first patient-specific exposure parameter and for the second patient-specific exposure parameter further to be based on the first patient-specific exposure parameter. For example, in this example embodiment, the second patient-specific exposure parameter can then correspond to the entire radiation dose absorbed by the patient as a result of medical examinations in that the radiation dose additionally absorbed as a result of the recording of the second image dataset MI.j is added to the first exposure parameter.

It is in particular also possible for the first patient-specific exposure parameter and/or the second patient-specific exposure parameter to be organ-specific exposure parameters, i.e. in this example embodiment to specify an absorbed radiation dose is for an organ of the patient. Alternatively, it is also possible for the first patient-specific exposure parameter and/or the second patient-specific exposure parameter to be a spatial distribution of the exposure relative to the patient coordinate system PCS.

The seventh step of the first example embodiment depicted of the method for providing a patient model PM.i, PM.j, PM.k is the provision PROV-PM.j of a second patient model PM.j of the patient P via the interface PU.i.IF, PU.j.IF, wherein the second patient model PM.j is a multi-parametric patient model and wherein the second patient model PM.j comprises the transformed second image dataset MI.j'.

In the example embodiment depicted, the second patient model PM.j comprises all the components of the first patient model PM.i and the second patient model PM.j comprises the modified first image dataset MI.i' and the transformed second image dataset MI.j'. The second patient model PM.j can therefore for example be defined by the following multi-parametric mapping:

$$PM.j: R^3 \to M_1 \times \ldots \times M_n \times M_{n+1} \times M_{1'};$$

$$\begin{pmatrix} x_1 \\ x_2 \\ x_3 \end{pmatrix} \mapsto \begin{pmatrix} f^{(1)}(x_1, x_2, x_3) \\ \vdots \\ f^{(n)}(x_1, x_2, x_3) \\ f^{(n+1)}(x_1, x_2, x_3) \\ f^{(1')}(x_1, x_2, x_3) \end{pmatrix}$$

If the optional step of the determination DET-MI.i' of a modified first image dataset MI.i' is not carried out, the second patient model PM.j is, for example, defined by the following multi-parametric mapping:

$$PM.i: R^3 \to M_1 \times \ldots \times M_n \times M_{n+1};$$

$$\begin{pmatrix} x_1 \\ x_2 \\ x_3 \end{pmatrix} \mapsto \begin{pmatrix} f^{(1)}(x_1, x_2, x_3) \\ \vdots \\ f^{(n)}(x_1, x_2, x_3) \\ f^{(n+1)}(x_1, x_2, x_3) \end{pmatrix}$$

Alternatively, it is also possible for the second patient model PM.j not to comprise all the components of the first patient model PM.i. The second patient model PM.j can in particular also comprise the second patient-specific exposure parameter when the step of the determination DET-PEP of a second patient-specific exposure parameter has been carried out.

FIG. 2 shows a second example embodiment of a method for providing a patient model PM.i, PM.j, PM.k of a patient P. The first step of the second example embodiment depicted is the reception REC-PM.i of a first patient model PM.i of the patient P via an interface PU.i.IF, PU.j.IF; this step can include all the advantageous embodiments and developments of the corresponding first example embodiment of a method for providing a patient model PM.i, PM.j, PM.k.

The second step of the second example embodiment depicted is the reception REC-RI of a registration image RI with the interface PU.i.IF, PU.j.IF. This step is an optional step. Herein, the registration image RI is a three-dimensional optical image of the patient, which was ascertained with a 3D camera. Herein, the 3D camera is firmly connected to the medical imaging apparatus MOD, MOD', therefore in particular the relationship between the coordinates relative to the 3D camera and the device coordinate system MCS is known.

The third step of the second example embodiment depicted is the determination of a transformation function TF via a calculating unit PU.i.CU, PU.j.CU, such as a processor for example, wherein the transformation function TF transfers a device coordinate system MCS of a medical imaging apparatus MOD, MOD' into the patient coordinate system PCS.

In this example embodiment, the transformation function TF is determined based on a three-dimensional optical image of the patient P as a registration image when the patient is arranged on a patient support apparatus of the medical imaging apparatuses MOD, MOD' for the performance of a medical imaging examination. Therefore, registration between the three-dimensional optical image and the first image dataset MI.i enables a transformation function TF to be determined, which can transfer the patient coordinate system PCS and the device coordinate system MCS into one other. In the second example embodiment depicted, the medical imaging apparatus MOD, MOD' is a computed tomography system.

Alternatively, it is also possible to determine a transformation function TF based on a scout view of the patient as a registration image when the patient is arranged on a patient support apparatus of the medical imaging apparatus MOD, MOD' for the performance of a medical imaging examination. If the medical imaging apparatus MOD, MOD' is a computed tomography system, the scout view is, for example, a topogram or a plurality of topograms ("scout view" is an English technical term). If the medical imaging apparatus MOD, MOD' is, for example, a magnetic-resonance tomography system, the scout view is, for example, a localizer scan ("localizer scan" is an English technical term). If the medical imaging apparatus MOD, MOD' is, for example, a positron-emission tomography system ("PET"), the overview recording can, for example, be an image dataset of a computed tomography system connected to the PET or an image dataset of a magnetic-resonance tomography system connected to the PET.

An optional step of the example embodiment depicted is the performance of imaging planning and/or automatic positioning based on the first patient model PM.i and the transformation function TF. For example, the image region of the second image dataset MI.j to be sampled can be ascertained based on the first patient model PM.i and based on the transformation function.

The fourth step of the second example embodiment depicted is the reception REC-RD of raw data via the interface PU.i.IF, PU.j.IF, wherein the raw data is based on an examination of the patient P via the medical imaging apparatus MOD, MOD'.

When, as in the example embodiment depicted, the medical imaging apparatus MOD, MOD' is a computed tomography system, the raw data is, for example, the X-ray attenuation coefficients relative to a plurality of directions through the patient P. On the other hand, if the medical imaging apparatus MOD, MOD' is a PET-Scanner, the raw data is positron events registered in the detectors. This raw data could be used as the sole basis for ascertaining a second image dataset MI.j; this process is called reconstruction. In computed tomography, known reconstruction algorithms are, for example, filtered back projection and iterative image reconstruction.

The recording of the raw data by the medical imaging apparatus MOD, MOD' can be based on the first patient model PM.i, in particular the amount and type of the raw data required for the imaging cab be determined based on the first patient model PM.i. Herein, in magnetic resonance tomography it is known to use planned undersampling to accelerate the image recording and to reduce the data volume known (a technical term is "compressed detection", English technical terms are "compressed sensing", "compressive sampling" or "sparse sampling"). Herein, in computed tomography it is in particular known to control the accelerating voltage of the X-ray tubes (an English technical term is "dose modulation").

The fifth step of the second example embodiment depicted is the determination DET-RC of a reconstruction constraint based on the first patient model PM.i, in particular based on the first image dataset MI.i, via the calculating unit/processor/processing circuitry PU.i.CU, PU.j.CU.

In the example embodiment depicted, the reconstruction constraint is the geometric shape of the patient, in other words, therefore, a segmentation of the first image dataset MI.i into patient regions and ambient regions. If the first image dataset MI.i is a computed tomography image dataset, this segmentation can be determined particularly efficiently using a threshold segmentation method, wherein, however, it is necessary to remove parts of the first image dataset MI.i that do not belong to the patient P, for example a patient bench.

In addition to the geometry of the patient, the reconstruction constraint can also be defined by the location of bones in the image region, which can subsequently be used to reduce scattered radiation in the case of a computed tomography recording. In addition, the reconstruction constraint can be defined by the location of metallic implants, which can also be used to reduce scattered radiation with computed tomography or to take account of magnetic-field inhomogeneities caused by the metallic implants in the case of magnetic resonance tomography. In the case of a PET recording, a reconstruction constraint can also be used for in addition attenuation correction ("attenuation correction" is an English technical term).

Since the reconstruction constraint was ascertained based on the first image dataset MI.i, the reconstruction constraint relates to the patient coordinate system PCS. Application of the transformation function TF or the inverse of the transformation function TF enables the reconstruction constraint also to be related to the device coordinate system MCS.

The sixth step of the second example embodiment depicted is the reconstruction RCN of the second image dataset MI.j based on the raw data and based on the reconstruction constraint via the calculating unit/processor/processing circuitry PU.i.CU, PU.j.CU.

In the example embodiment depicted, reconstruction RCN including the reconstruction constraint is performed by iterative reconstruction, which can generally be applied for raw data from different medical imaging apparatuses MOD, MOD', in particular computed tomography systems, magnetic-resonance tomography systems and positron-emission tomography systems. The algorithm for iterative reconstruction generates an iterative sequence of temporary first image datasets and herein minimizes a cost function with a first parameter and a second parameter, wherein the first parameter relates to the deviation of a back projection from a temporary image dataset and the raw data and wherein the second parameter relates to the deviation of the temporary image dataset and from the reconstruction constraint. If there is a plurality of reconstruction constraints, it is also possible to use a plurality of second parameters. Another name for the first parameter is "quality parameter", another name for the second parameter is "regularization parameter" or "constraint".

The regularization parameter R used can, for example, be the sum of the squared deviations from the first image dataset MI.i and the temporary image dataset:

$$R(f, g) = \sum_{i,j,k} (f_{ijk} - g_{ijk})^2$$

$$R(f, g) = \int \int \int (f(x_1, x_2, x_3) - g(x_1, x_2, x_3))^2 dx_1 dx_2 dx_3$$

Alternatively, as in the example embodiment depicted, the regularization parameter can also be based on the geometry of the patient anatomy (which was, for example, ascertained by way of threshold segmentation)

$$R(f, g) = \sum_{i,j,k} (Seg(f)_{ijk} - Seg(g)_{ijk})^2$$

$$R(f, g) = \int \int \int (Seg(f)(x_1, x_2, x_3) - Seg(g)(x_1, x_2, x_3))^2 dx_1 dx_2 dx_3$$

Such iterative reconstruction is not restricted to a case in which the first image dataset MI.i and the second image dataset MI.j were recorded by the same type of medical imaging apparatus MOD, MOD' (i.e. for example in each case by a computed tomography system). For example, level sets ("level set" is an English technical term) or the edges of level sets and their directions can be used to improve the contrast of the resultant second image dataset MI.j.

Generally, the regularization parameter can also be used without a reconstruction constraint, for example to smooth noise, in that the regularization parameter corresponds to the total variance of the temporary image dataset or a sum of local image gradients.

In the example embodiment depicted, the reconstruction RCN of the second image dataset MI.j is performed relative to the device coordinate system MCS. Alternatively, it is possible, based on the transformation function TF, to perform the reconstruction RCN of the second image dataset MI.j directly relative to the patient coordinate system PCS.

The seventh step of the second example embodiment depicted is the determination DET-MI.j' of a transformed second image dataset MI.j' based on the second image dataset MI.j and the transformation function TF via the calculating unit/processor/processing circuitry PU.i.CU, PU.j.CU. When, as in the example embodiment depicted, the second image dataset MI.j was reconstructed relative to the device coordinate system MCS, this step of the second example embodiment corresponds to the corresponding step of the first example embodiment and can have all the same advantageous embodiments and developments. If, alternatively, the second image dataset MI.j was reconstructed relative to the patient coordinate system PCS, the step of the determination DET-MI.j' of a transformed second image dataset MI.j' can be dispensed with then, in other words, the step of the determination DET-MI.j' of a transformed second image dataset MI.j' is then identical to the step of the reconstruction RCN of the second image dataset MI.j since the second image dataset MI.j and the transformed second image dataset MI.j' are identical.

The eighth step of the second example embodiment depicted of the method for providing a patient model PM.i, PM.j, PM.k is the determination DET-MI.i' of a modified first image dataset MI.i' based on the first image dataset MI.i and the transformed second image dataset MI.j' via the calculating unit/processor/processing circuitry PU.i.CU, PU.j.CU. The seventh step of the determination DET-MI.i' of a modified first image dataset MI.i' is an optional step. This step of the second example embodiment corresponds to the corresponding step of the first example embodiment and can all have all the same advantageous embodiments and developments.

The ninth step of the second example embodiment depicted of the method for providing a patient model PM.i, PM.j, PM.k is the provision PROV-PM.j of a second patient model PM.j of the patient P via the interface PU.i.IF, PU.j.IF, wherein the second patient model PM.j is a multi-parametric patient model and wherein the second patient model PM.j comprises the transformed second image dataset MI.j'. This step of the second example embodiment corresponds to the corresponding step of the first example embodiment and can all have all the same advantageous embodiments and developments.

FIG. 3 shows a third example embodiment of a method for providing a patient model PM.i, PM.j, PM.k of a patient P. The steps of the reception REC-PM.i of a first patient model PM.i of the patient P, the reception REC-RI of a registration image, the determination of a transformation function TF, the determination DET-RC of a reconstruction constraint, the reconstruction RCN of the second image dataset MI.j, the determination DET-MI.j' of a transformed second image dataset MI.j', the determination DET-MI.i' of a modified first image dataset MI.i' and the provision PROV-PM.j of a second patient model PM.j of the third example embodiment correspond to the corresponding steps of the second example embodiment and can have all the same advantageous embodiments and developments.

Unlike the second example embodiment, the third example embodiment also comprises the step of the determination DET-PIP of the patient-specific image-recording parameter based on the first image dataset MI.i via the calculating unit/processor/processing circuitry PU.i.CU, PU.j.CU.

For all the medical imaging apparatuses MOD, MOD' (in particular with a computed tomography system, a magnetic-resonance tomography system and/or a positron-emission tomography system), the patient-specific image-recording parameter can in particular be an image-recording region (another term is "scan region"), a sectional image position, sectional orientation, patient positioning and/or a patient-bench position. It is known from the prior art to adjust such patient-specific image-recording parameters manually, in particular based on a registration image RI.

The first image dataset MI.i or the first patient model PM.i and the transformation function TF can be used as the basis for registering the medical imaging apparatus with the scanner. This registration can, for example during imaging of the heart, be used as the basis for the automatic definition of the start position of the patient support and the image-recording region based on the position of the heart in the first image dataset MI.i. During imaging of the heart, the main axes of the heart can also be determined in the first image dataset MI.i and the sectional image position and the sectional image orientation can be defined such that this corresponds to prespecified standards. Similarly, the sectional image position and/or the sectional image orientation can be determined automatically during an imaging examination of the head or the spine automatically. Alternatively, the manual definition of the scan parameters can also be performed using the first image dataset MI.i, this implies that no scout view (for example, topogram) has to be recorded for the manual definition of the scan parameters.

In the example embodiment depicted, the image-recording parameter is a spatially-resolved maximum radiation dose for the patient. The spatially-resolved maximum radiation dose can also be interpreted as an image dataset relative to the patient coordinate system PCS, which in each case assigns a maximum radiation dose to coordinates of the patient. In the example embodiment depicted, the maximum radiation dose is ascertained based on the first image dataset MI.i in that different organs of the patient P are segmented based on the first image dataset MI.i. For these different organs, in each case, a maximum dose is known or specified in guidelines (a technical term is "tolerance dose" or "maximum/minimum tolerance dose"), which can be used directly or in a fraction in the spatially-resolved maximum radiation dose of the organ. The spatially-resolved maximum radiation dose can then be used as a target dose or maximum dose in a medical imaging examination via a computed tomography system.

If the medical imaging apparatus MOD, MOD' is a magnetic-resonance tomography system, the patient-specific image-recording parameter can in particular a spatially-resolved maximum heating of the patient. For example, it is possible to ensure during each imaging via magnetic resonance tomography that the radio-frequency radiation emitted by the radio-frequency unit MOD.4 that is absorbed in the patient P only results in a maximum heating of the tissue of 1° C. It is already known from the prior art to perform numerical simulations based on the height and the weight of the patient in order to derive limit values for the intensity of the radio-frequency radiation or for the duration of the examination. The models on which these numerical simulations are based are very simple (for example, a patient P is described by a cylinder) and it is, therefore, necessary to add or subtract high tolerance values during the determination of the limit values. These tolerance values then restrict the imaging performance of the magnetic-resonance tomography system. However, if the numerical simulations are performed based on the first image dataset MI.i, the tolerance values can be selected much lower and hence the performance of the scanner improved.

In contrast to the second example embodiment, the third example embodiment also comprises the step of the provision PROV-PIP of the patient-specific image-recording parameter via the interface PU.i.IF, PU.j.IF. In this example embodiment, the image-recording parameter, i.e. here the spatially-resolved maximum radiation dose, is sent to the medical imaging apparatus, i.e. the computed tomography system.

The computed tomography system then takes account of the spatially-resolved maximum radiation dose in its treatment planning. In particular, the X-ray voltage and/or the X-ray current is adapted for each direction through the patient P such that the prespecified spatially-resolved maximum radiation dose is not exceeded at each point of the patient P.

If the medical imaging apparatus MOD, MOD' is a magnetic-resonance tomography system, the patient-specific image-recording parameter can also relate to spatially-resolved B1 inhomogeneities ("B1 inhomogeneities" is an English technical term) or dielectric characteristics of the patient P. B1 inhomogeneities (another English technical term is "shadow artifacts") occur due to dielectric effects in the patient P. Known for the suppression of these B1 inhomogeneities is the "parallel transmit" method ("pTX", a German translation is "Parallelanregung"—literally "parallel excitation") that uses multiple and simultaneous radio-frequency channels in order to adapt the B1 magnetic field of the body coil ("body coil" is an English technical term) such that the B1 inhomogeneities are counteracted. The first image dataset MI.i can be used as the basis for determining the dielectric characteristics of the patient P, which are in particular based on the distribution of fatty tissue, water and bone regions. Based on the dielectric characteristics, it is then in particular possible for the radio-frequency pulses of the different radio-frequency channels to be modulated in order to counteract the B1 inhomogeneities. It is then in particular also possible to take account of the spatially-resolved heating of the patient P during the determination of the modulation of the radio-frequency pulses.

Alternatively, in the case of magnetic resonance tomography, the patient-specific image-recording parameter can be correction data for shimming the main magnetic field (i.e. for the correction of B0 inhomogeneities). B0 inhomogeneities occur as the result of interactions between the main magnetic field and the patient's body due to the susceptibility. It is known from the prior art to determine the correction data based on a calibration recording with the magnetic-resonance tomography system. Based on the first image dataset MI.i or the first patient model, the correction data for shimming can be determined without a calibration recording, for example by way of numerical simulations, the correction data can then be used during image recording in order to correct the B0 inhomogeneities via a correction coil.

Alternatively, in the case of magnetic resonance tomography, the patient-specific image-recording parameter can also be based on the excitation of nerve fibers of the patient P. The excitation of the nerve fibers (an English technical term is "peripheral nerve stimulations") occurs due to quickly changing gradient fields and can result in discomfort or involuntary movements of the patient P. It is therefore known to select the amplitude and the rate of change of the gradient fields such that perceptible excitation of the nerve fibers can be reliably excluded. However, the first image dataset MI.i or the first patient model PM.i can also be used as the basis for determining the course of the nerve fibers of the patient P and, for example by numerical simulations, to set the limit values for the amplitude and the rate of change of the gradient fields specifically for the patient P to be examined or the body region to be examined.

Figure 4:
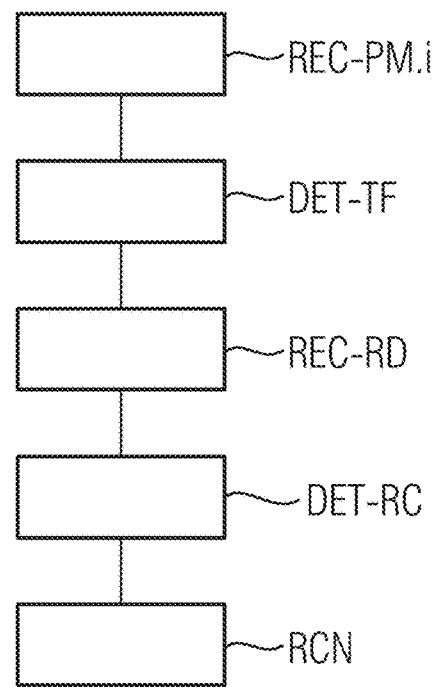
FIG. 4 shows an example embodiment of a method for reconstructing an image dataset.

FIG. 4 shows an example embodiment of a method for reconstruction RCN of an image dataset. In the example embodiment depicted, the method comprises the steps of the reception REC-PM.i of a first patient model PM.i of the patient P, the determination DET-TF of a transformation function TF, the reception REC-RD of raw data, the determination DET-RC of a reconstruction constraint and the reconstruction RCN of the second image dataset MI.j. These steps of an example embodiment of a method for the reconstruction RCN of an image dataset correspond to the corresponding steps of the second example embodiment of a method for providing a patient model PM.i, PM.j, PM.k and can have the same advantageous embodiments and developments.

Figure 5:
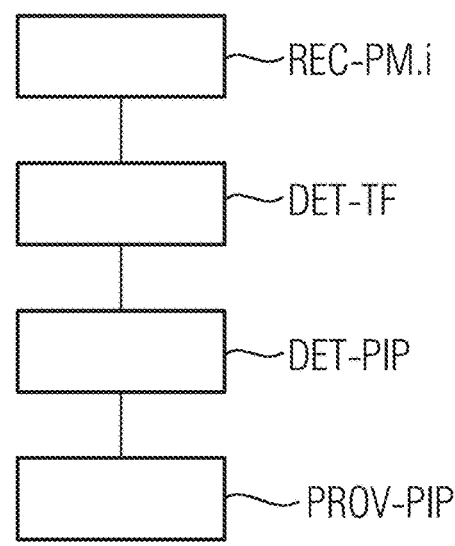
FIG. 5 shows an example embodiment of a method for providing a patient-specific image-recording parameter.

FIG. 5 shows an example embodiment of a method for providing a patient-specific image-recording parameter. In the example embodiment depicted, the method comprises the steps of the reception REC-PM.i of a first patient model PM.i of the patient P, the step of the determination DET-PIP of the patient-specific image-recording parameter and the step of the provision PROV-PIP of the patient-specific image-recording parameter. These steps of an example embodiment of a method for providing a patient-specific image-recording parameter correspond to the corresponding steps of the third example embodiment of a method for providing a patient model PM.i, PM.j, PM.k and have the same advantageous embodiments and developments.

Figure 6:
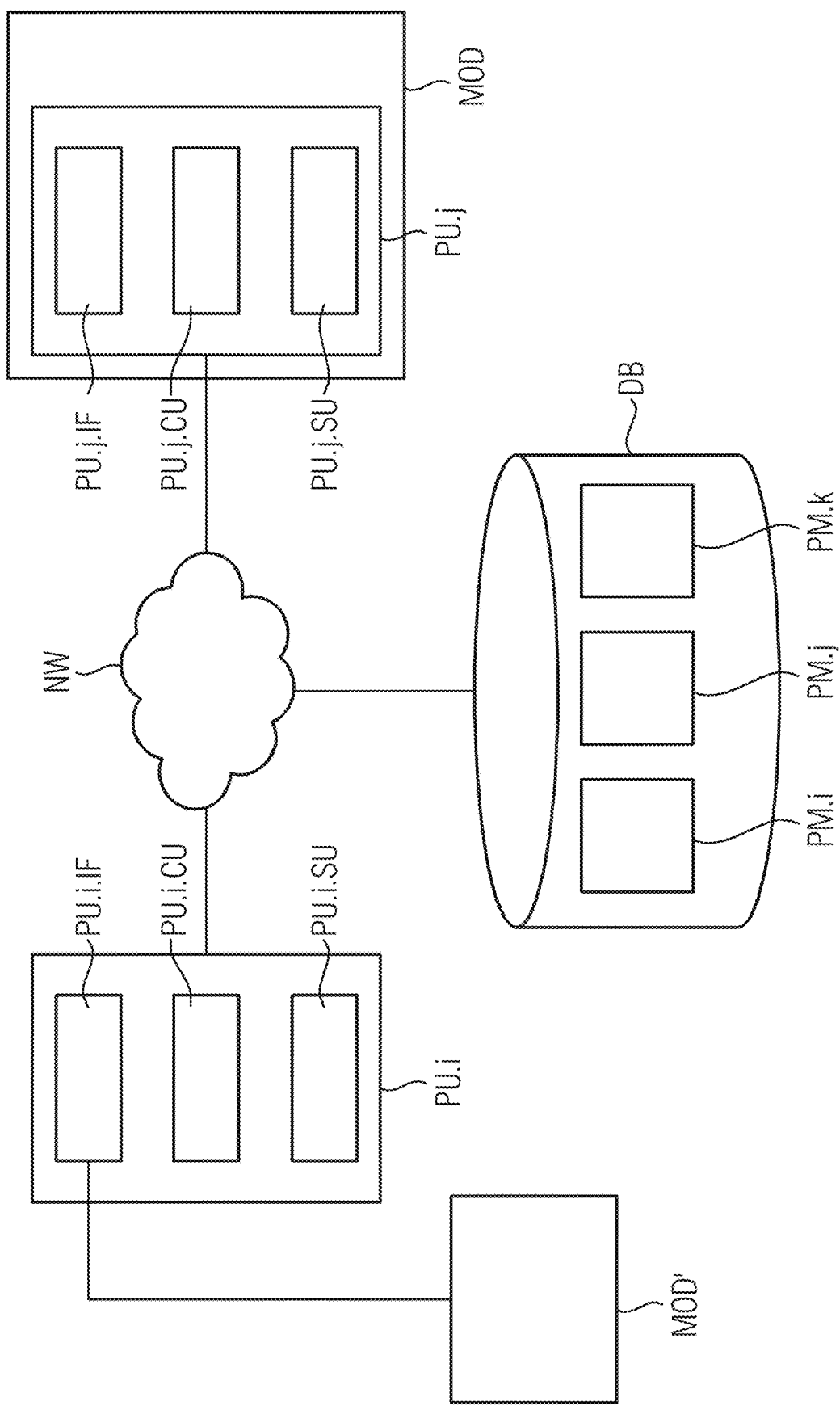
FIG. 6 shows a providing unit for providing a patient model.

FIG. 6 shows a first providing unit PU.i and a second providing unit PU.j for providing a patient model PM.i, PM.j, PM.k. Each of the providing units PU.i, PU.j depicted here is configured to carry out a method according to the invention. These providing units PU.i, PU.j in each case comprise an interface PU.i.IF, PU.j.IF, a calculating unit/processor/processing circuitry PU.i.CU, PU.j.CU, such as a processor for example and a storage unit PU.i.SU, PU.j.SU, such as a memory for example. Optionally, these providing units PU.i, PU.j can also in each case comprise an input and output unit.

Each of the providing units PU.i, PU.j can in particular be a computer, a microcontroller or an integrated circuit. Alternatively, each of the providing units PU.i, PU.j can be a real or virtual group of computers (an English technical term for a real group is "cluster", an English technical term for a virtual group is "cloud"). An interface PU.i.IF, PU.j.IF can be a hardware or software interface (for example PCI-Bus, USB or Firewire). The calculating unit PU.i.CU, PU.j.CU can comprise hardware elements or software elements, for example a processor such as a microprocessor or a so-called FPGA ("Field Programmable Gate Array") or other processing circuitry. A storage unit PU.i.SU, PU.j.SU can be implemented as a non-permanent main memory (random access memory, RAM for short) and/or permanent mass storage device (hard disk, USB stick, SD card, solid state disk). An input and output unit comprises at least one input unit and/or at least one output unit.

In the example embodiment depicted, the first providing unit PU.i is separate from a medical imaging apparatus MOD', but embodied, for example via the interface PU.i.IF, to receive image datasets, in particular DICOM-image datasets from the medical imaging apparatus MOD'. The first providing unit PU.i depicted can, therefore, in particular expand the functionality of an existing imaging apparatus MOD'. In addition, in the example embodiment depicted, the second providing unit PU.j is integrated in a medical imaging apparatus MOD. Therefore, without any additional expansion, the integration of the second providing unit PU.j endows the medical imaging apparatus MOD with the functionality required to carry out a method according to the invention.

The providing units PU.i, PU.j are connected by a network NW to one another and to a database DB.

The network NW can be a local area network ("local area network" is an English technical term, "LAN" for short) or a wide-area network ("wide-area network" is an English technical term, "WAN" for short). An example of a local area network is an intranet, an example of a wide area network is the internet. The network NW can in particular also be wireless, in particular as a WLAN ("wireless LAN", the abbreviation "WiFi" is common in English) or as a Bluetooth connection. The network NW can also be embodied as a combination of the examples given.

The database DB can in particular be embodied as a dedicated database server, however, it can also be embodied as database applications operated on one or more of the providing units PU.i, PU.j. Herein, the database DB can in particular be embodied as a relational database, which can, for example, be requested by way of SQL ("structured query language" in English, "Strukturierte Abfragesprache" in German). However, the database DB can also be embodied as a non-relational database. In particular, the database DB can be a distributed database based on a block chain.

The first providing unit PU.i depicted and the second providing unit PU.j depicted can in each case also be embodied as a reconstruction unit for the reconstruction of an image dataset and as a providing unit for providing a patient-specific image-recording parameter.

Figure 7:
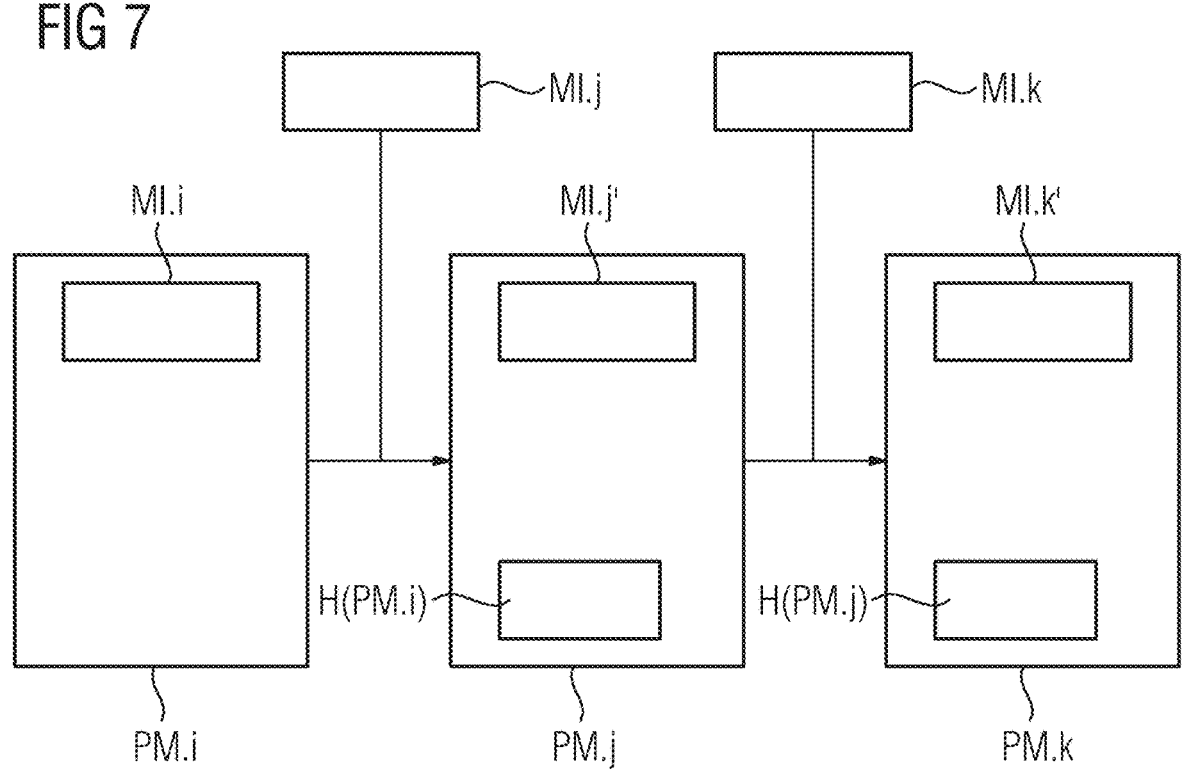
FIG. 7 shows a first example embodiment of the data structure of the patient models.
Figure 8:
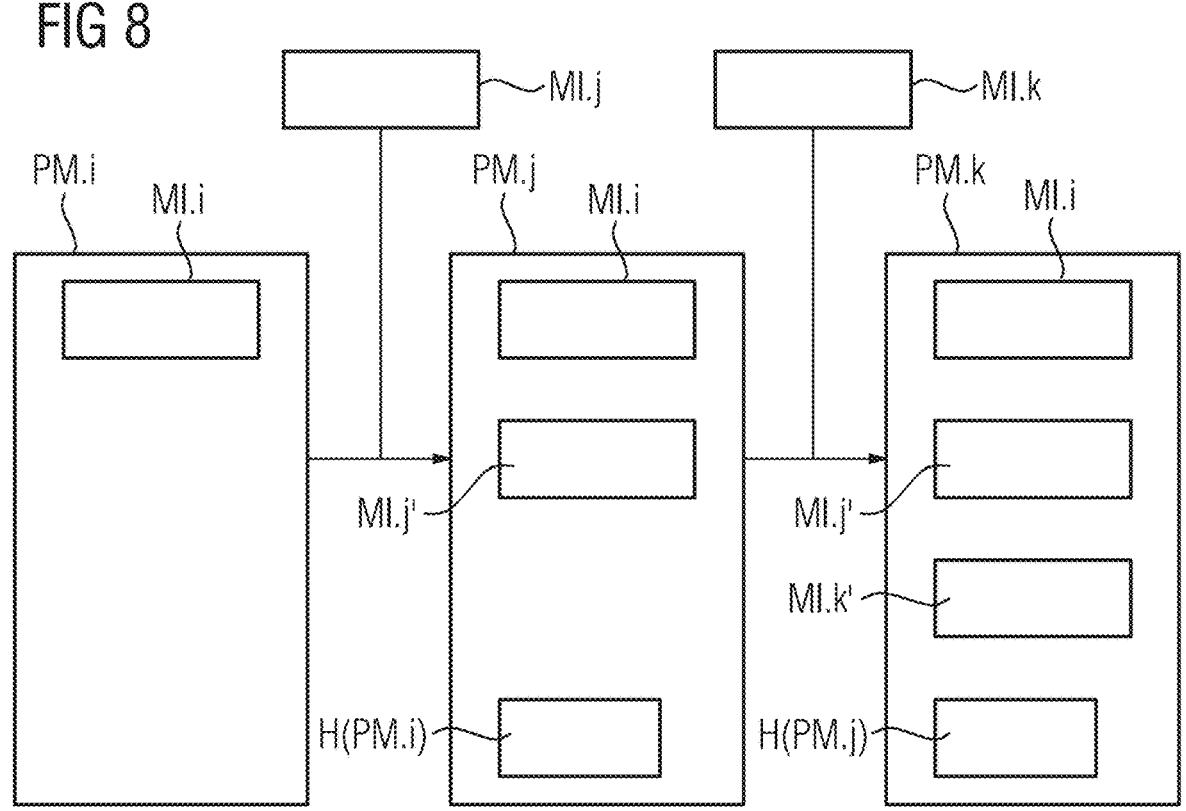
FIG. 8 shows a second example embodiment of the data structure of the patient models.
Figure 9:
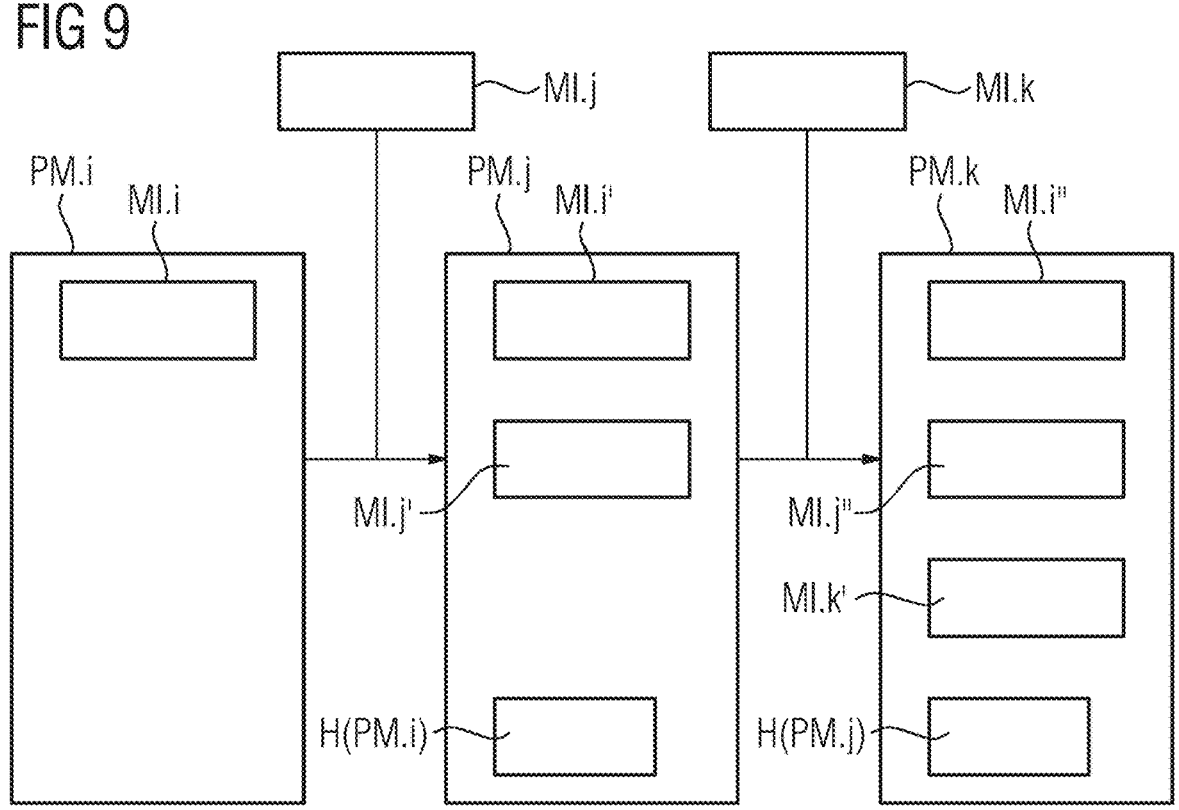
FIG. 9 shows a third example embodiment of the data structure of the patient models.

FIG. 7 shows a first example embodiment of the data structure of the patient models PM.i, PM.j, PM.k. FIG. 8 shows a second example embodiment of the data structure of the patient models PM.i, PM.j, PM.k. FIG. 9 shows a third example embodiment of the data structure of the patient models PM.i, PM.j, PM.k. Herein, in each case a dual embodiment of the method for providing a patient model PM.i, PM.j, PM.k is visualized. In the first embodiment, a second patient model PM.j is determined and provided on the basis of a first patient model PM.i, of a first image dataset MI.i and a second image dataset MI.j. in the second embodiment, a second patient model PM.k is determined and provided on the basis of a first patient model PM.j, a second image dataset MI.j' and a second image dataset MI.k. Generally, therefore, a plurality of patient models PM.i, PM.j, PM.k can be arranged in a chain, wherein the chain indicates the temporal sequence of the different patient models PM.i, PM.j, PM.k and wherein, due to the method according to the invention, sequential patient models PM.i, PM.j, PM.k originate from one another.

In all three example embodiments, the second patient model PM.j, PM.k in each case comprises the transformed second image dataset MI.j'. In addition, in all three example embodiments, the second patient model PM.j, PM.k advantageously comprises a hash value H(PM.i), H(PM.j) of the associated first patient model PM.i, PM.j. Herein, a hash value H(PM.i), H(PM.j) is the application of a cryptographic hash function or a one-way variance function to the first patient model PM.i, PM.j.

In the second example embodiment depicted in FIG. 8, the second patient model PM.j, PM.k in each case also comprises the associated first image dataset MI.i, MI.j'. This additional information in the second patient model PM.j, PM.k makes all available information available in each case in the chronologically last patient model, so that it is not necessary to access any further stored patient models to access previous information.

In the third example embodiment depicted in FIG. 9, the second patient model PM.j, PM.k in each case also comprises the associated modified first image dataset MI.i', MI.j''. This enables previous information that has been adapted to the present structure of the patient P to be provided quickly.

In particular, the first patient model PM.i, PM.j and the second patient model PM.j, PM.k can be stored as datasets in a block chain when the second patient model PM.j, PM.k comprises a hash value H(PM.i), H(PM.j) of the associated first patient model PM.i, PM.j. Advantageously, each patient model PM.i, PM.j, PM.k then also comprises a freely selectable parameter (for example a natural number) adapted such that the hash value H(PM.i), H(PM.j), H(PM.j) satisfies a prespecified condition, for example lower than a prespecified threshold. Only when this condition is satisfied does a program logic allow the patient model PM.i, PM.j, PM.k to be attached to the block chain as a further block. In particular, therefore, a plurality of computing operations is necessary in order to determine a suitable freely selectable parameter. This can advantageously resolve the consensus problem ("consensus problem" is an English technical term).

It is also possible to combine the second and the third example embodiment so that the second patient model PM.j, PM.k in each case also comprises the associated first image dataset MI.i, MI.j' and the associated modified first image dataset MI.i', MI.j''. This enables the above-described advantages of the second and the third example embodiment to be achieved simultaneously.

Figure 10:
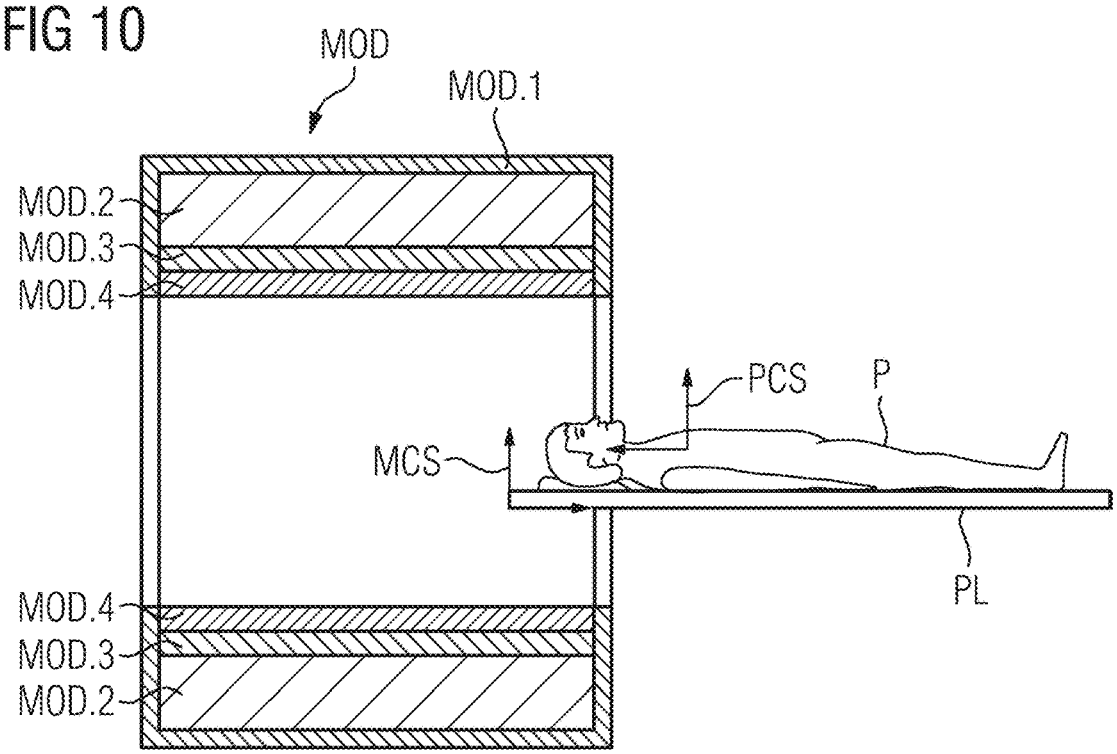
FIG. 10 shows a medical imaging apparatus.

FIG. 10 shows a medical imaging apparatus MOD using the example of a magnetic-resonance tomography system. In this example embodiment, the medical imaging apparatus comprises a magnet unit MOD.1 with a housing, the magnet unit MOD.1 in turn comprises a basic magnet MOD.2, a gradient unit MOD.3 and a radio-frequency antenna unit MOD.4. A patient P can be moved into an examination chamber of the medical imaging apparatus MOD via a patient bench PL. In addition, Fig. X depicts a patient-coordinate system PCS and a device coordinate system MCS. In this example embodiment, the origin of the device coordinate system MCS is a point of the patient bench PL and the axes of the device coordinate system MCS are orthogonal. This means in particular that the device coordinate system MCS can be moved relative to the magnet unit MOD.1, but the positional relationship between the device coordinate system MCS and the magnet unit MOD.1 is known from the position of the patient bench PL. The origin of the patient coordinate system PCS is located in the xiphoid process (the Latin technical term is "Processus xiphoideus") of the breastbone (the Latin technical term is "Sternum"), a first axis of the patient coordinate system PCS extends from the origin in the upward direction, a second axis of the patient coordinate system PCS extends from the origin in the downward direction, a third axis of the patient coordinate system PCS extends from the origin in lateral direction, all three axes are in each case orthogonal in pairs.

Figure 11:
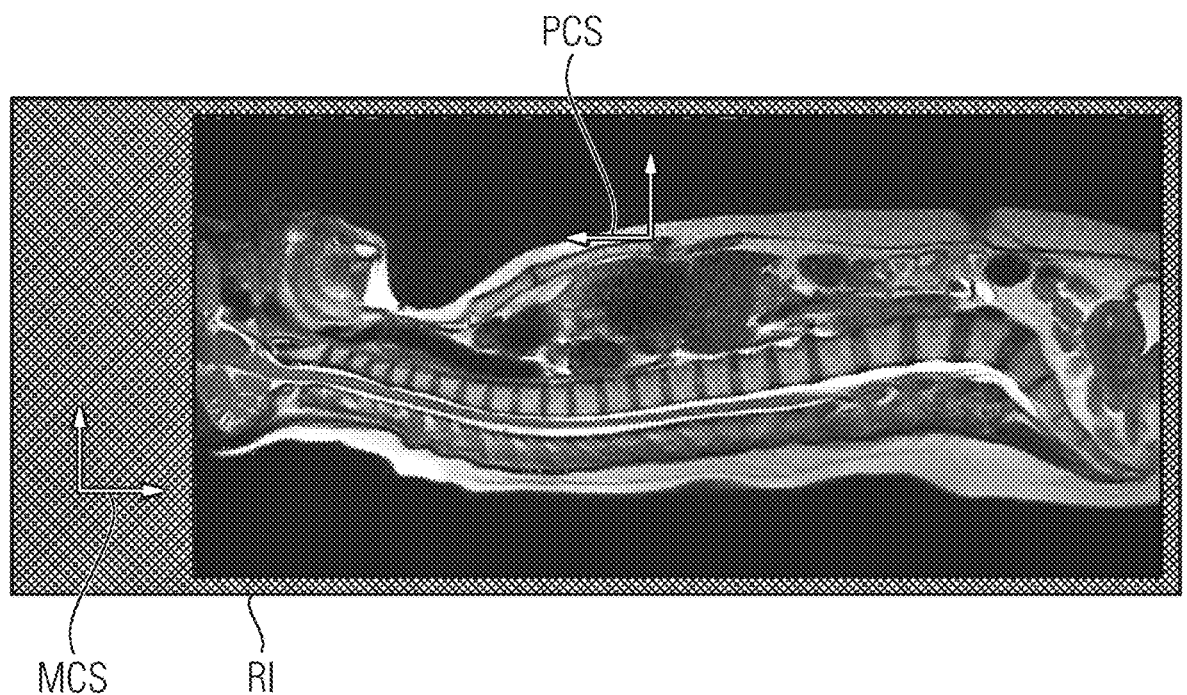
FIG. 11 shows a registration image.

FIG. 11 shows an example embodiment of a registration image RI. Herein, the registration image RI is a location recording, which was recorded via a magnetic-resonance tomography system. In this example embodiment, the registration image RI is a two-dimensional image, however, a registration image RI can also be a three-dimensional image, alternatively, a registration image can also comprise a plurality of individual images. FIG. 11 also shows the device coordinate system MCS and the patient coordinate system PCS, both coordinate systems MCS, PCS are defined as in FIG. 10. The patient coordinate system PCS in FIG. 11 corresponds to the application of the transformation function TF to the device coordinate system MCS, wherein the transformation function TF was ascertained by a registration of the first image dataset MI.i with the registration image RI. As depicted in FIG. 11, it is not a necessary requirement for an intensity value to be assigned to each pixel or each voxel of the registration image.

Figure 12:
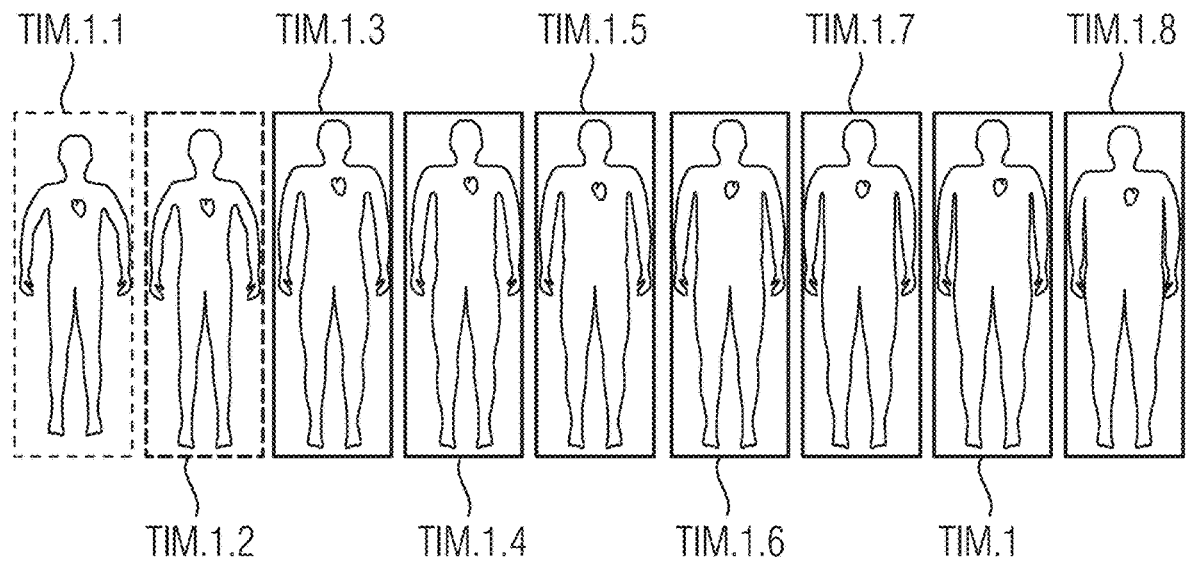
FIG. 12 shows a template-image dataset and adapted template-image datasets.
Figure 13:
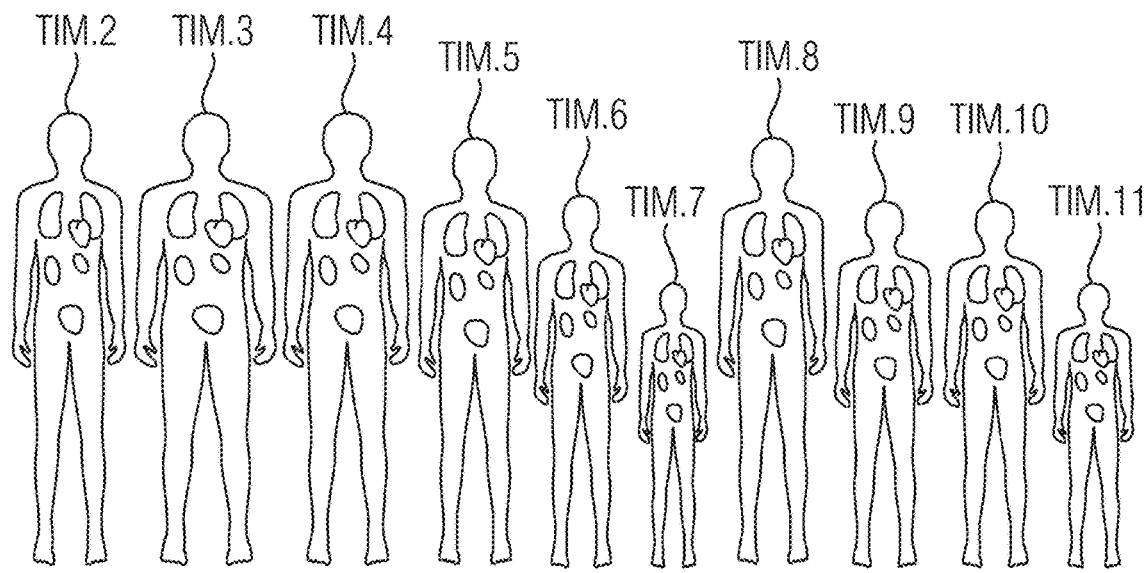
FIG. 13 shows further template-image datasets.

FIG. 12 shows an example embodiment of a first image dataset MI.i based on a template-image dataset TIM.1, wherein a template-image dataset TIM.1 is not an image dataset of the patient P, but an image dataset of another patient or an artificial image dataset. Herein, FIG. 12 shows an image dataset TIM.1 of another patient with a body mass index ("BMI" for short) of 37. The BMI of the patient P can be used as the basis for adapting the template-image dataset TIM.1. Herein, FIG. 12 shows image datasets adapted for different BMIs (TM.1.1 for BMI 18, TM.1.2 for BMI 23, TM.1.3 for BMI 24, TM.1.4 for BMI 26, TM.1.5 for BMI 28, TM.1.6 for BMI 31, TM.1.7 for BMI 34 and TM.1.8 for BMI 41). Alternatively, a template-image dataset TIM.1 can also be adapted based on another patient parameter (for example height, weight, body fat component, age, gender). In particular, a template-image dataset TIM.1 can also be adapted based on a three-dimensional optical image of the patient, herein the adaptation of the template-image dataset TIM.1 can be performed similarly to the step of the determination DET-MI.i' of a modified first image dataset MI.i'. FIG. 13 shows further template-image datasets TIM.2, . . . , TIM.11, which can be selected for other patient parameters and adapted based on the patient parameter. FIG. 13 shows template-image datasets TIM.2, . . . , TIM.11 for other age groups, genders and body sizes.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing a patient model of a patient, the method comprising:
   receiving a first patient model of the patient via an interface, the first patient model including a first image dataset of the patient, the first image dataset being coordinated relative to a first coordinate system;
   receiving a second image dataset of the patient via the interface, the second image dataset being based on a medical imaging apparatus and being coordinated relative to a second coordinate system;
   determining, via at least one of a processor or processing circuitry, a transformation function to transform the second coordinate system into the first coordinate system;
   determining, via the at least one of the processor or processing circuitry, a transformed second image dataset based on the second image dataset and the transformation function;
   determining, via the at least one of the processor or processing circuitry, a modified first image dataset by adapting the first image dataset to an anatomy of the patient associated with the transformed second image dataset; and
   providing, via the interface, a second patient model of the patient, the second patient model including the modified first image dataset.

2. The method of claim 1, wherein the second patient model includes the modified first image dataset and the transformed second image dataset.

3. The method of claim 1, wherein the transformation function is based on a comparison of the first image dataset to the second image dataset.

4. The method of claim 1, further comprising:
   receiving a registration image via the interface, wherein the transformation function is based on the registration image.

5. The method of claim 4, wherein the registration image is a three-dimensional optical image of the patient, the three-dimensional optical image being recorded with an optical image recording unit and the optical image recording unit being arranged on the medical imaging apparatus.

6. The method of claim 1, further comprising:
   determining, via the at least one of the processor or processing circuitry, a patient-specific image-recording parameter based on the first image dataset; and
   providing the patient-specific image-recording parameter via the interface.

7. The method of claim 1, wherein
   the receiving a second image dataset is performed after the determining of the transformation function; and
   the receiving a second image dataset includes
      receiving raw data via the interface, the raw data based on an examination of the patient via the medical imaging apparatus,
      determining, via the at least one of the processor or processing circuitry, a reconstruction constraint based on the first patient model, and
      reconstructing, via the at least one of the processor or processing circuitry, the second image dataset based on the raw data and the reconstruction constraint.

8. The method of claim 1, wherein the first image dataset is a template-image dataset and the template-image dataset is selected based on a patient parameter of the patient.

9. The method of claim 1, further comprising:
   determining, via the at least one of the processor or processing circuitry, a patient-specific exposure parameter based on the transformed second image dataset.

10. The method of claim 1, wherein the second patient model comprises a hash value of the first patient model.

11. A providing unit for providing a patient model, the providing unit comprising:
   an interface configured to
      receive a first patient model of a patient, the first patient model including a first image dataset of the patient, the first image dataset being coordinated relative to a first coordinate system,
      receive a second image dataset of the patient, the second image dataset being based on a medical imaging apparatus and being coordinated relative to a second coordinate system, and
      provide a second patient model of the patient, the second patient model including a modified first image dataset; and
   at least one of a processor or processing circuitry configured to determine a transformation function to transform the second coordinate system into the first coordinate system, determine a transformed second image dataset based on the second image dataset and the transformation function, and determine the modified first image dataset by adapting the first image dataset to an anatomy of the patient associated with the transformed second image dataset.

12. The providing unit of claim 11, wherein the second patient model includes the modified first image dataset and the transformed second image dataset.

13. A medical imaging apparatus comprising:
a providing unit for providing a patient model, the providing unit including
an interface configured to
receive a first patient model of a patient, the first patient model including a first image dataset of the patient, the first image dataset being coordinated relative to a first coordinate system, receive a second image dataset of the patient, the second image dataset being based on the medical imaging apparatus and being coordinated relative to a second coordinate system, and provide a second patient model of the patient, the second patient model including a modified first image dataset, and at least one of a processor or processing circuitry configured to
determine a transformation function to transform the second coordinate system into the first coordinate system, determine a transformed second image dataset based on the second image dataset and the transformation function, and determine the modified first image dataset by adapting the first image dataset to an anatomy of the patient associated with the transformed second image dataset.

14. A non-transitory computer program product storing a computer program directly loadable into a memory, the computer program including program sections for carrying out a method for providing a patient model of a patient when the program sections are executed by at least one processor, the method comprising:
receiving a first patient model of the patient via an interface, the first patient model including a first image dataset of the patient, the first image dataset being coordinated relative to a first coordinate system;

receiving a second image dataset of the patient via the interface, the second image dataset being based on a medical imaging apparatus and being coordinated relative to a second coordinate system;

determining a transformation function to transform the second coordinate system into the first coordinate system;

determining a transformed second image dataset based on the second image dataset and the transformation function;

determining a modified first image dataset by adapting the first image dataset to an anatomy of the patient associated with the transformed second image dataset; and providing a second patient model of the patient, the second patient model including the modified first image dataset.

15. A non-transitory computer-readable storage medium storing program sections, which are readable and executable by at least one processor to carry out a method for providing a patient model of a patient when the program sections are executed by the at least one processor, the method comprising:
receiving a first patient model of the patient via an interface, the first patient model including a first image dataset of the patient, the first image dataset being coordinated relative to a first coordinate system;

receiving a second image dataset of the patient via the interface, the second image dataset being based on a medical imaging apparatus and being coordinated relative to a second coordinate system;

determining a transformation function to transform the second coordinate system into the first coordinate system;

determining a transformed second image dataset based on the second image dataset and the transformation function;

determining a modified first image dataset by adapting the first image dataset to an anatomy of the patient associated with the transformed second image dataset; and providing a second patient model of the patient, the second patient model including the modified first image dataset.

16. The method of claim 7, wherein the determining, via the at least one of the processor or processing circuitry, a reconstruction constraint based on the first patient model, comprises:
determining the reconstruction constraint based on the first image dataset.

17. The method of claim 3, further comprising:
determining, via the at least one of the processor or processing circuitry, a patient-specific image-recording parameter based on the first image dataset; and providing the patient-specific image-recording parameter via the interface.

18. The method of claim 3, wherein
the receiving a second image dataset is performed after the determining of the transformation function; and
the receiving a second image dataset includes
receiving raw data via the interface, the raw data based on an examination of the patient via the medical imaging apparatus, determining, via the at least one of the processor or processing circuitry, a reconstruction constraint based on the first patient model; and reconstructing, via the at least one of the processor or processing circuitry, the second image dataset based on the raw data and the reconstruction constraint.

19. The method of claim 3, wherein the first image dataset is a template-image dataset and the template-image dataset is selected based on a patient parameter of the patient.

20. The method of claim 3, further comprising:
determining, via the at least one of the processor or processing circuitry, a patient-specific exposure parameter based on the transformed second image dataset.

21. The method of claim 3, wherein the second patient model comprises a hash value of the first patient model.

22. The non-transitory computer program product of claim 14, wherein the transformation function is based on a comparison of the first image dataset to the second image dataset.

23. The non-transitory computer-readable storage medium of claim 15, wherein the transformation function is based on a comparison of the first image dataset to the second image dataset.

24. The method of claim 1, wherein the adapting adapts the first image dataset to conform to the anatomy of the patient associated with the transformed second image dataset to determine the modified first image dataset.

* * * * *